(12) United States Patent
Kishikawa et al.

(10) Patent No.: US 7,251,029 B2
(45) Date of Patent: Jul. 31, 2007

(54) BIREFRINGENCE MEASUREMENT APPARATUS, STRAIN REMOVER, POLARIMETER AND EXPOSURE APPARATUS

(75) Inventors: Yasuhiro Kishikawa, Tochigi (JP); Seiji Takeuchi, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 461 days.

(21) Appl. No.: 10/610,986

(22) Filed: Jun. 30, 2003

(65) Prior Publication Data

US 2004/0008348 A1  Jan. 15, 2004

(30) Foreign Application Priority Data

Jul. 1, 2002 (JP) ............... 2002-191706
Dec. 27, 2002 (JP) ............... 2002-380014

(51) Int. Cl.
  *G01J 4/00* (2006.01)
(52) U.S. Cl. ..................................... 356/364
(58) Field of Classification Search ..................... None
  See application file for complete search history.

(56) References Cited

U.S. PATENT DOCUMENTS

| | | | |
|---|---|---|---|
| 3,463,575 A | 8/1969 | Gates, Jr. | |
| 4,252,410 A | 2/1981 | Jain | |
| 5,077,803 A * | 12/1991 | Kato et al. | 382/124 |
| 5,398,112 A | 3/1995 | Ai et al. | |
| 5,475,491 A | 12/1995 | Shiozawa | |
| 5,719,702 A | 2/1998 | Decker | |
| 5,784,202 A | 7/1998 | Noguchi | |
| 5,825,492 A * | 10/1998 | Mason | 356/491 |
| 6,008,497 A | 12/1999 | Mizoguchi et al. | |
| 6,124,064 A | 9/2000 | Ozawa | |
| 6,157,448 A | 12/2000 | Kowa et al. | |
| 6,252,650 B1 | 6/2001 | Nakamura | |
| 6,473,179 B1 | 10/2002 | Wang et al. | |

FOREIGN PATENT DOCUMENTS

| | | |
|---|---|---|
| JP | 4-102178 | 4/1992 |
| JP | 7-320090 | 12/1995 |
| JP | 8-221595 | 8/1996 |
| JP | 11-96394 | 4/1999 |
| JP | 11-328427 | 11/1999 |
| WO | WO 99/42796 | 8/1999 |

OTHER PUBLICATIONS

Ho et al., Neutral and color-selective beam splitting assemblies with polarization-independent intensities, Jul. 1, 1992, Applied Optics, vol. 31, No. 10, pp. 3813-3820.

* cited by examiner

*Primary Examiner*—Tu T. Nguyen
(74) *Attorney, Agent, or Firm*—Morgan & Finnegan LLP

(57) ABSTRACT

A birefringence measurement apparatus for calculating information of polarization of light emitted from an object to be measured includes a light source, a first polarization element for extracting a beam in a specific polarization direction from light emitted from the light source, a sample stage that holds an object to be measured, at least one beam splitting unit that splits the light emitted from the object into two beams having the same polarization as that of the light emitted from the object, at least two second polarization elements for extracting beams in a specific polarization direction of the light split by the beam splitting unit, at least two light-quantity detectors for detecting light quantity of beams that have transmitted through the second polarization element, and an operation part for operating a light quantity received by the light-quantity detectors.

23 Claims, 24 Drawing Sheets

BIREFRINGENCE MEASUREMENT APPARATUS, STRAIN REMOVER, POLARIMETER AND EXPOSURE APPARATUS

This application claims a benefit of foreign priority based on Japanese Patent Applications No. 2002-191706, filed on Jul. 1, 2002, and Japanese Patent Application No. 2002-380014, filed on Dec. 27, 2002, each of which is hereby incorporated by reference herein in its entirety as if fully set forth herein.

BACKGROUND OF THE INVENTION

The present invention relates to a birefringence measurement apparatus for calculating a retardation magnitude and an azimuth of a principal axis of an object retardance to be measured, a strain remover having the birefringence measurement apparatus, a polarimeter or polarization detector that includes the birefringence measurement apparatus, and an exposure apparatus that includes the polarimeter.

As the need for smaller and thinner electronic apparatuses grows in recent years, finer semiconductor devices mounted in these electronic apparatuses have been increasingly demanded, and various proposals have been made for higher exposure resolution to fulfill this demand.

Since a shortened wavelength of an exposure light source is one effective means for higher resolution, the recent exposure light source has shifted from a g-line (with a wavelength of about 436 nm) and an i-line (with a wavelength of about 365 nm) to a KrF excimer laser (with a wavelength of about 248 nm) and an ArF excimer laser (with a wavelength of about 193 nm). In the near future, use of an $F_2$ excimer laser (with a wavelength of approximately 157 nm) is expected to be promising.

A conventional optical element is available to an optical system down to a wavelength region for the i-line, but conventional optical glass cannot be used for such a wavelength region as covers the KrF and ArF excimer lasers and the $F_2$ laser due to its low transmittance. Therefore, an optical system in an exposure apparatus that uses the excimer laser as a light source has commonly used an optical element made of quartz glass ($SiO_2$) or calcium fluoride ($CaF_2$) having larger transmittance to light with a shortened wavelength, and it has been considered that exposure apparatus that uses the $F_2$ laser as a light source necessarily uses an optical element made of calcium fluoride.

Calcium fluoride single crystal has been manufactured mainly by a crucible descent method or Bridgman method. This method fills highly purified materials of chemical compounds in a crucible, melts in a growth device, and gradually descends the crucible, thereby crystallizing the materials from the bottom of the crucible. The heat history in this growth process remains as a stress in calcium fluoride crystal. Calcium fluoride exhibits birefringence to the stress. The residual stress deteriorates optical performance. In order to reduce the retardation magnitude as little as possible which results from the existing residual stress or strain amount, a heat treatment has been conventionally used to reduce or remove the residual stress from the optical element.

The strain removing method heats up an optical element under a desired condition up to the preset temperature of viscous fluidity region where the optical element exhibits structurally viscous fluid flows viscously and structural change, holds the preset temperature for a predetermined period of time to mitigate temporary strain due to permanent strain and rapid rise in temperature, and then gradually cools the optical element under a gradual change condition that may maintain the mitigated strain down to temperature which does not provide a structural change, followed by natural cooling.

Birefringence is one influential factor to imaging performance of an exposure apparatus. As elucidated by NIST's publication in May of 2001, calcium fluoride, which is used for an optical system in an exposure apparatus that utilizes ArF excimer laser, $F_2$ laser, etc. as an exposure light source, includes intrinsic birefringence that results from its crystal structure, in addition to stress birefringence that results from an internal stress (or stress strain). Therefore, cares for birefringence including the intrinsic birefringence becomes critical in developing an exposure apparatus. They require a grasp of the retardation magnitude of the exposure wavelength. In addition, a measurement of the residual birefringence in the optical element is essential to the strain removal. A conventional birefringence measurement method includes a rotary analyzer method, a phase compensation method that utilizes a Babinet compensator, etc., a Senarmont method that utilizes a quarter-wave plate, a phase modulation method that utilizes a photoelastic modulator ("PEM"), and an optical heterodyne method that uses a Zeeman laser etc. as a light source.

A demand for the reduced residual stress in the optical element has become increasingly strict for recent more precise optical systems and denser semiconductor devices, and the conventional birefringence measurement methods have faced difficulties in measuring the residual birefringence in the optical element with satisfactory precision. In addition, the conventional birefringence measurement methods cannot easily measure birefringence characteristics in an ultraviolet region of calcium fluoride etc., when using ultraviolet light as a measurement light source, due to the unstable light source and the manufacture difficulties of a PEM and a phase shifter, such as a quarter-wave plate for a measurement wavelength. Moreover, long-term research and development activities are necessary to establish heat treatment conditions of optical elements, and the long-term heat treatment are required to reduce the residual stress in the optical element. This deteriorates the productivity of the optical element, and causes an increase of production cost.

BRIEF SUMMARY OF THE INVENTION

Accordingly, it is an exemplified object of the present invention to provide a birefringence measurement apparatus that may easily, quickly, and precisely measure the birefringence characteristic in an ultraviolet region of an object to be measured.

Another object of the present invention is to provide a birefringence measurement apparatus that may easily and precisely measure retardation magnitude of an optical element, such as an intrinsic birefringence caused by a crystal structure and birefringence caused by a residual stress.

Still another object of the present invention is to provide a strain remover that may control the birefringence as well as shortening the heat treatment time to remove the residual birefringence in an optical element.

It is yet another object of the present invention is to provide an exposure apparatus that includes a polarimeter that has the above birefringence measurement apparatus.

A birefringence measurement apparatus of one aspect of the present invention for calculating information of polar ization of light emitted from an object to be measured includes a light source, a first polarization element for extracting a beam in a specific polarization direction from light emitted from the light source, a sample stage that holds an object to be measured, at least one beam splitting unit that splits the light emitted from the object into two beams having the same polarization as that of the light emitted from the object, at least two second polarization elements for extracting beams in a specific polarization direction of the light split by the beam splitting unit, at least two light-quantity detectors for detecting light quantity of beams that have transmitted through the second polarization element, and an operation part for operating a light quantity received by the light-quantity detectors.

The light source may be a pulsed light source, such as an excimer laser. The first polarization element may include a linear polarizer. The birefringence measurement apparatus may further include a rotating mechanism for rotating the first polarization element around an optical axis. The birefringence measurement apparatus may further include a rotating mechanism for rotating the object on the sample stage around an optical axis. The birefringence measurement apparatus may further include a measurement position varying mechanism for varying a measurement range of the object on the sample stage. The birefringence measurement apparatus may further include a mechanism for inserting the object into and removing the object from the beam to be measured.

The beam splitting unit may split incident light into two beams while maintaining polarization of the incident light. The second polarization element is a linear polarizer. The birefringence measurement apparatus may further include a rotating mechanism for rotating the second polarization element around an optical axis. The second polarization element may be in crossed nicols to the first polarization element. The second polarization element may be in parallel nicols to the first polarization element.

The operation part may analyze polarization changes of the light emitted from the object based on an output result of the light-quantity detector to the rotational angle of the object. The operation part may analyze polarization changes of the light emitted from the object based on an output result of light-quantity detector to rotational angles of the first and second elements.

The birefringence measurement apparatus may calculate a retardation magnitude and an azimuth of a principal axis of the object retardance based on polarization changes of the light emitted from the object, which has been analyzed by the operation part. The birefringence measurement apparatus may calculate a retardation magnitude and an azimuth of a principal axis of the object retardance by feeding back polarization changes of the light emitted from the object, which has been analyzed by the operation part, to the rotating mechanism.

The birefringence measurement apparatus may further include rotating mechanisms for rotating the first and second polarization elements, wherein the birefringence measurement apparatus calculates a retardation magnitude and an azimuth of a principal axis of the object retardance by feeding back polarization changes of the light emitted from the object, which has been analyzed by the operation part, to the rotating mechanism.

A strain remover of another aspect of the present invention that removes strain generated during a manufacture process of an optical element as an object includes a heat treatment part that heat treats the optical element, and a birefringence measurement apparatus for calculating information of polarization of light emitted from the object, the birefringence measurement apparatus including a light source, a first polarization element for extracting a beam in a specific polarization direction of light from the light source, a sample stage that holds the object, at least one beam splitting unit that splits the light emitted from the object into two beams having the same polarization with the light, at least two second polarization elements for extracting beams in a specific polarization direction of the light split by the beam splitting unit, at least two light-quantity detectors for detecting light quantity of beam that has transmitted through the polarization element, and an operation part for operating a light quantity received by the light-quantity detectors.

The strain remover may further include a controller that controls heat treatment conditions for the optical element so that retardation magnitude of the optical element is within a predetermined range, by measuring the retardation magnitude of the optical element during the heat treatment and feeding back the heat treatment part.

A polarimeter of another aspect of the present invention that calculates polarization information of incident light includes at least one beam splitter unit that splits the incident light into two beams having the same polarization as the incident light, at least two polarization elements, a rotary mechanism for rotationally controlling the polarization element, at least two light-quantity detectors, and an operation part that operates light quantity received by the light-quantity detector.

A polarimeter of still another aspect of the present invention includes an apparatus that uses the incident light, at least one beam splitter unit that splits the incident light into two beams having the same polarization as incident light, one beam being used for the apparatus, and the other beam being used to calculate polarization information of the incident light, at least two polarization elements, a rotary mechanism for rotationally controlling the polarization element, at least two light-quantity detectors, and an operation part that operates light quantity received by the light-quantity detector. The polarization information of the incident light may be fed back to the apparatus. The incident light may be pulsed light.

An exposure apparatus of another aspect of the present invention includes a light source, at least one beam splitter unit that splits incident light from the light source into two beams having the same polarization as incident light, one beam being used for exposure, and the other beam being used to calculate polarization information of the incident light, at least two polarization elements, a rotary mechanism for rotationally controlling the polarization element, at least two light-quantity detectors, and an operation part that operates light quantity received by the light-quantity detector. The exposure apparatus may further include a controller for controlling exposure parameters based on the polarization information. An exposure apparatus may further include a controller for controlling the light source based on the polarization information. The light source may be a pulsed light source, such as an excimer laser.

A birefringence measurement apparatus of another aspect of the present invention for measuring birefringence in an object to be measured includes a light source part that emits light having specific polarization to the object, a polarization element that may rotationally convert and maintain polarization of light that has passed through the object, a beam splitter unit that splits light emitted from the object into two or more beams to be measured, while maintaining polarization of the light, a first optical system that extracts a beam having a predetermined polarization direction from the beam to be measured, using the polarization element, a light-quantity detector that detects light quantity of the beam to be measured, from the first optical system, and a controller for calculating the retardation magnitude of the object based on the light quantity of the beam to be measured, which is detected by the light-quantity detector.

The controller may calculate an azimuth of a principal axis of the object retardance based on the light quantity of the beam to be measured, which is detected by the light-quantity detector. The birefringence measurement apparatus may further include a second optical system that extracts a beam having a predetermined polarization direction after a phase of polarization of the beam to be measured is converted. The controller may distinguish a fast axis and a slow axis of principal axes of the object retardance from each other. The specific polarization may be circularly polarized light.

The light source part may include a light source that emits a beam having arbitrary polarization, a linear polarizer that is oriented with its polarization direction at 0° relative to a baseline axis, and a quarter-wave plate that is oriented with a fast axis at 45° relative to the baseline axis at the linear polarizer. The light source may be a pulsed light source, such as an excimer laser.

The birefringence measurement apparatus may further include a stage that holds the object and enables the object to move relative to the light emitted from the light source part. The polarization element has a half-wave plate that may be rotatable around an optical axis. The beam splitter unit may include three parallel plates. The first optical system may have a linear polarizer. The linear polarizer may be oriented with its polarization direction at 0° relative to a preset baseline axis around an optical axis on a baseline axis.

The first optical system may include a first linear polarizer that is oriented with its polarization direction at 0° relative to a baseline axis, and a second polarizer that is oriented so that the second polarizer has its polarization direction in a crossed nicols with the polarization direction of the first linear polarizer. The second optical system may extract the beam having the predetermined polarization direction after the phase of polarization of the beam to be measured is converted by 90°.

The second light system may include a quarter-wave plate that is oriented with a fast axis at 45° relative to a baseline axis, and a linear polarizer that is oriented with its polarization direction at 45° relative to the baseline axis.

A birefringence measurement apparatus of another aspect of the present invention for measuring birefringence in an object retardance to be measured includes a light source part that emits light having circularly polarized light to the object, a polarization element that may rotationally convert and maintain polarization of light that has passed through the object, an optical system that extracts a beam of a predetermined polarization direction from and converts a phase of light emitted from the polarization element, a light-quantity detector that detects light quantity of light that has passed through the optical system, and a controller for calculating the retardation magnitude and an azimuth of a principal axis of the object retardance based on the light quantity of the light which is detected by the light-quantity detector. The controller may distinguish a fast axis and a slow axis of principal axes of the object retardance from each other.

A measuring method of another aspect of the present invention includes the steps of introducing light having a circularly polarized light to an object to be measured, splitting light from the object into first and second beams while maintaining polarization of the light from the object, detecting changes in light quantity of the first and second beams when the light from the object is rotationally converted, and calculating a retardation magnitude and azimuth of a principal axis of the object retardance based on the changes in light quantity of the first and second beams.

The calculating step simultaneously may calculate the retardation magnitude and azimuth of a principal axis of the object retardance. The measuring method may further include rotationally converting the first and second beams, and determining a fast or slow axis of a principal axis of the object retardance. The calculating step calculates the retardation magnitude and azimuth of a principal axis of the object retardance based on amplitudes and phases of light quantities of the first and second beams.

A strain remover includes the above birefringence measurement apparatus, and a heat treatment part to heat-treat an object and reduces a birefringence in the object, which has been measured by the birefringence measurement apparatus. The strain remover may further include a controller for controlling the heat treatment part so that the retardation magnitude of the object may be within a predetermined range.

A polarimeter of another aspect of the present invention for measuring polarization of light includes a beam splitter unit that splits the light into at least two beams while maintaining the polarization of the light, an optical system that extracts a beam in a predetermined polarization direction from the beam, a light-quantity detector for detecting a light quantity of the beam from the optical system, and a controller for operating polarization of the light based on the light quantity of the beam detected by the light-quantity detector.

A device fabrication method of another aspect of this invention includes the steps of exposing a plate by using the above exposure apparatus, and performing a predetermined process for the exposed object. Claims for a device fabrication method for performing operations similar to that of the above exposure apparatus cover devices as intermediate and final products. Such devices include semiconductor chips like an LSI and VLSI, CCDs, LCDs, magnetic sensors, thin film magnetic heads, and the like.

Other objects and further features of the present invention will become readily apparent from the following description of the embodiments with reference to accompanying drawings.

DETAILED DESCRIPTION OF THE PREFERRED EMBODIMENTS

First Embodiment

Figure 1:
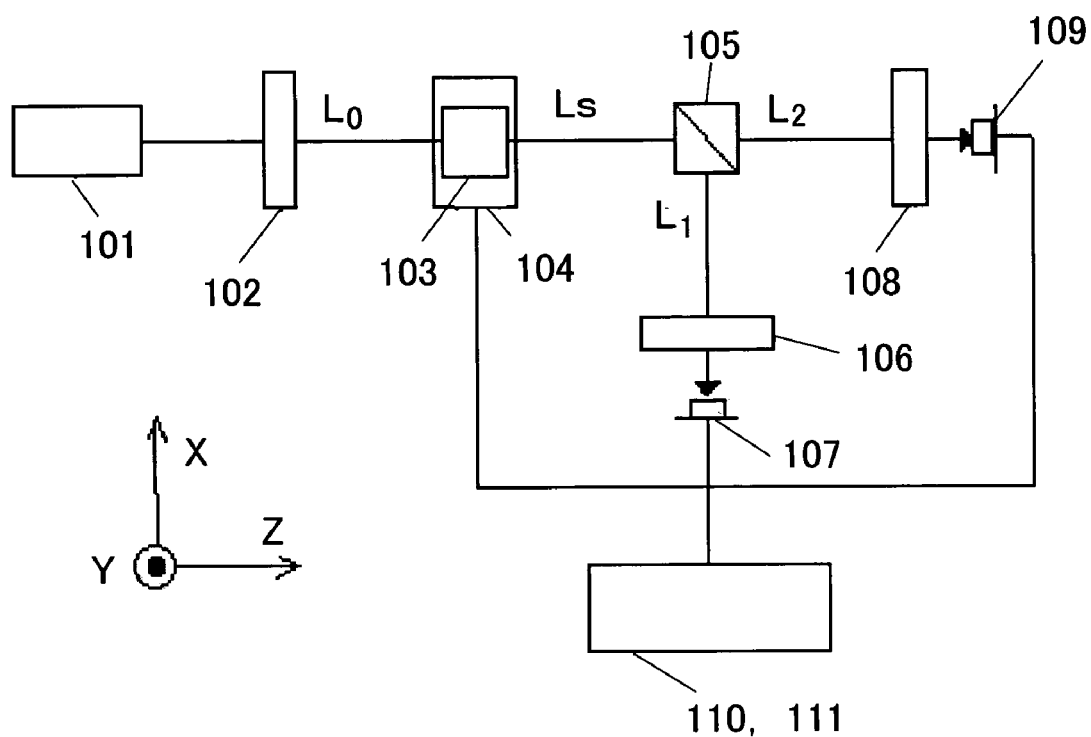
FIG. 1 is a view of a birefringence measurement apparatus of a first embodiment.

FIG. 1 is a schematic view of a structure of a birefringence measurement apparatus of a first embodiment according to the present invention. A description will be given of this birefringence measurement apparatus of the first embodiment with reference to FIGS. 1, 2 and 3.

FIG. 1 sets a Z-axis as a proceed direction of light emitted from a light source 101, an X-axis as a direction perpendicular to the Z-axis on a laser installation surface, and a Y-axis as a direction normal to the laser installation surface.

In FIG. 1, the birefringence measurement apparatus of the first embodiment includes a light source 101, a polarization element 102, an object to be measured 103, a sample stage 104, a beam splitter means 105, polarization elements 106 and 108, light-quantity detector means 107 and 109, an operation part 110, and a controller 110.

The light emitted from the light source 101 is incident upon the object 103 after converted into a linearly polarized light $L_0$ via the polarization element 102 that is oriented with a polarization direction at 0° to a baseline axis present on the XY surface.

Here, the polarization elements 102, 106 and 108 may use an optical element that separates orthogonal linearly polarized light components and picks up one linearly polarized light component, such as a Glan-Thompson polarizing prism, a Rochon polarizing prism, a Senarmon polarizing prism, and a Wollaston polarizing prism or a polarization beam splitter made of dielectric multilayer, etc.

The sample stage 104 has a rotary mechanism, a rotation around the optical axis of which is controlled by a stepping motor, etc. The stepping motor is controlled based on a command of the controller 111, and one cycle of birefringence measurement is a rotation from 0° to 180° (or 0° to 360°) in the azimuth of the fast axis relative to the baseline axis.

The sample stage 104 has a measurement position varying mechanism, such as an XY stage, which may variably control a measurement position manually or automatically on a surface orthogonal to the optical-axis direction. In other words, the sample stage 104 may measure the two-dimensional birefringence distribution on the measurement surface.

The beam splitter means 105 has a beam splitter unit (shown in FIG. 2) including three parallel plates, which serves to divide light into two beams while maintaining the polarization of the incident light. The light Ls that has birefringence information of the object 103 is split by the beam splitter means 105 into beams $L_1$ and $L_2$ while the polarization of the light Ls is maintained.

The beam $L_1$ is incident upon the light-quantity detector means 107 through the polarization element 106 that is oriented relative to the polarization element 102 so that the polarization direction is in parallel nicols.

The beam $L_2$ is incident upon the light-quantity detector means 109 through the polarization element 108 that is oriented relative to the polarization element 102 so that the polarization direction is in crossed nicols.

The light-quantity detector means 107 and 109 detect these light signals which include the birefringence information of the object 103, i.e., a retardation magnitude and an azimuth of a principal axis, and output detection signals corresponding to the light intensities of the light signal to the operation part 110 on a real-time basis.

The operation part 110 and controller 111 store a CPU and a memory, and control actions of each component in the birefringence measurement apparatus, such as the light source 101 and sample stage 104. By executing a preset operational algorithm based on the detection signals detected by the light-quantity detector means 107 and 109, a phase difference Δ and an azimuth of fast axis Φ are operated and the operational result of the birefringence measurement is output to an output unit (not shown).

A description will be given of the beam splitter means that maintains the polarization with reference to FIG. 2.

Figure 2:
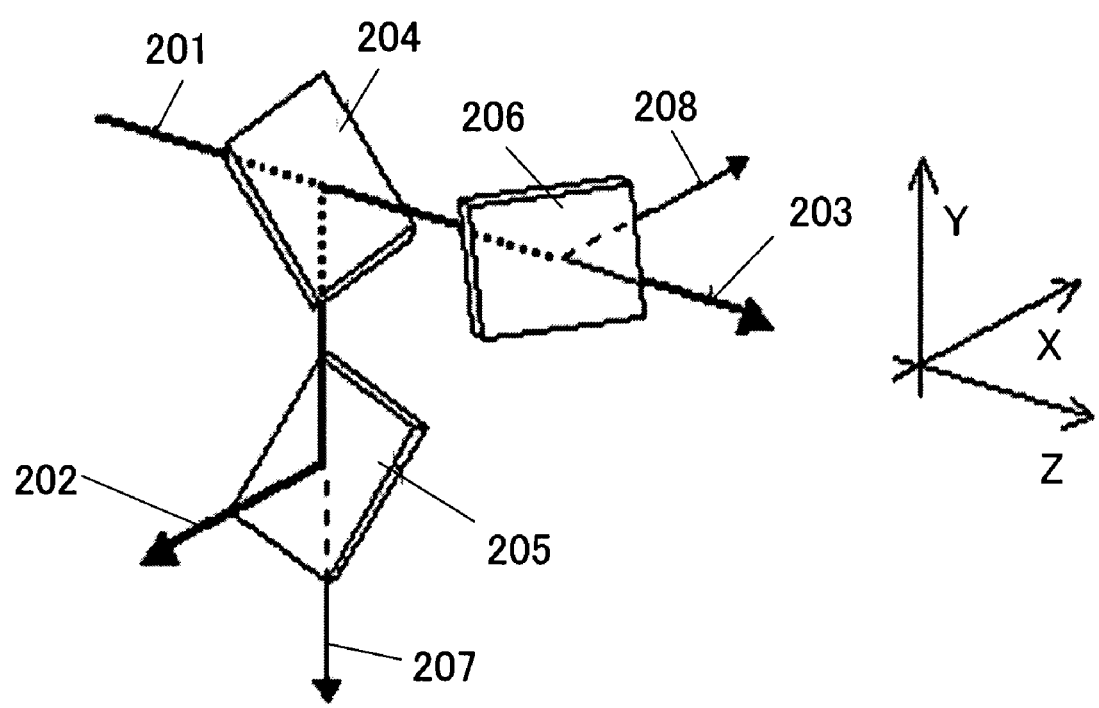
FIG. 2 is a view of a beam splitter in the first embodiment.

FIG. 2 is a view for explaining the beam splitter means that splits the incident light into two beams that have the same polarization as the incident light. 201 is incident light, 204, 205, and 206 are parallel plates arranged so that light may be incident at an angle of 45°, 202 is a first beam that reflects twice on two parallel plates, and 203 is a second beam that transmits both parallel plates. 207 and 208 are unnecessary light in this embodiment.

The first parallel plate 204 and the second parallel plate 205 are arranged so that the p-polarized component incident upon the first parallel plate 204 may reflect as s-polarized component on the second parallel plate 205. According to this arrangement, a polarization component on the second parallel plate 205, which has reflected as an s-polarized component on the first parallel plate 204.

The third parallel plate 206 is arranged so that a p-polarized component, which has transmitted through the first parallel plate 204, transmits as an s-polarized component through the third parallel plate 206.

A description will be given of a principle by which the beam splitter means splits the incident light into two beams that have the same polarization as the incident light. A reflection on the rear surface of the parallel plate is ignored for simplicity purposes.

When the incident light is completely polarized light, the electric field vector is expressed as Equation 1:

$$E = E_p + E_s \quad (1)$$

The incident light is split for calculation into the linear polarized component $E_p$ as the p-polarized component upon reflection on the first parallel plate and the linear polarized component $E_s$ as the s-polarized component upon reflection on the first parallel plate. When the incident light is partially polarized light or unpolarized light, it may be considered as an aggregate of plural completely polarized beams, and each completely polarized light is maintained.

When three parallel plates made of the same material are used, these three parallel plates have the same complex amplitude reflectance $r_p$ and $r_s$ of the p-polarized light and s-polarized light. Then, the complex amplitude $E_{11}$ as a first polarized component of the first beam 202 that has reflected twice on parallel plates is expressed as in Equation 2:

$$E_{11} = r_s r_p E_p \quad (2)$$

where $E_p$ is a complex amplitude of the linear polarized component as the p-polarized light upon reflection on the first parallel plate, and $E_s$ is a complex amplitude of the linear polarized component as the s-polarized light upon reflection on the first parallel plate.

The second polarized component of the complex amplitude $E_{12}$ is expressed as in Equation 3:

$$E_{12} = r_p r_s E_s \quad (3)$$

The complex amplitude $E_1$ of reflected light as a sum of them is expressed as in Equation 4:

$$E_1 = r_s r_p (E_p + E_s) \quad (4)$$

Since it is light as the incident light multiplied by constant $r_s r_p$, and this first beam 202 is the same polarization as the incident light. Complex amplitude $E_{21}$ of first polarized light of the second beam 203 that has transmitted the parallel plate twice will be given as in Equation (5):

$$E_{21} = t_s t_p E_p \quad (5)$$

Complex amplitude $E_{22}$ of second polarized light is expressed as in Equation (6):

$$E_{22} = t_p t_s E_s \quad (6)$$

Complex amplitude $E_2$ of the transmitting light as a sum of them is expressed as in Equation (7):

$$E_2 = t_s t_p (E_p + E_s) \quad (7)$$

Since it is light as the incident light multiplied by constant $t_s t_p$, and this second beam 203 is the same polarization as the incident light.

While the incident light has an incident angle of 45° relative to the parallel plate, the angle is not limited to 45° when the three incident angles are the same. The similar effect is available when such three beam splitting elements as a grating and a beam splitter are used which have the same splitting characteristics, such as reflection and transmission characteristics. $r_s$, $r_p$, $t_p$ and $t_s$ may not necessarily be simple real constants, but be complex constants that exhibit a phase change when a splitter with a film is used.

Although FIG. 1 does not show unnecessary light, beams 207 and 208 in FIG. 2 would cause stray light and thus are absorbed by a beam damper.

The constants $r_s$, $r_p$, $t_p$ and $t_s$ may be calculated or measured in advance for corrective operation.

A description will be given of a birefringence measuring method of a first embodiment according to the present invention with reference to FIG. 1.

The light emitted from the light source 101 is converted into linear polarized light via the polarization element 102 that is oriented with a polarization direction at 0° to a baseline axis present. A Jones matrix of the polarization element 102 is given by Equation 8. Where beam $L_o$ is light emitted from the polarization element 102, the polarization is expressed by Equation 9 and the Jones matrix:

$$P_H = \begin{pmatrix} 1 & 0 \\ 0 & 0 \end{pmatrix} \quad (8)$$

$$E_o = \begin{pmatrix} 1 \\ 0 \end{pmatrix} \quad (9)$$

The beam $L_o$ transmits through the object 103, and is converted into elliptical polarized light that occurs due to a phase offset resulting from a difference of refractive index of two principal axes of the object 103, i.e., a fast axis and a slow axis. The phase difference $\Delta$ and the azimuth of the principal axis $\Phi$ of the object 103 and the Jones matrix of the object 103 are expressed as in Equation 10:

$$S = \begin{pmatrix} \cos(\phi) & -\sin(\phi) \\ \sin(\phi) & \cos(\phi) \end{pmatrix} \quad (10)$$

$$\begin{pmatrix} \exp(i*\Delta/2) & 0 \\ 0 & \exp(-i*\Delta/2) \end{pmatrix} \begin{pmatrix} \cos(\phi) & \sin(\phi) \\ -\sin(\phi) & \cos(\phi) \end{pmatrix}$$

The object 103 rotates around the optical axis by the sample stage 104. Where $\theta$ is a rotational angle, the Jones matrix of this rotary conversion is expressed as in Equation 11.

$$R_\theta = \begin{pmatrix} \cos(\theta) & -\sin(\theta) \\ \sin(\theta) & \cos(\theta) \end{pmatrix} \quad (11)$$

The Jones matrix of the object 103 is expressed as in Equation 12:

$$S_{rot} = R_\theta \times S \times R_{-\theta} \quad (12)$$

The polarization of exit light $L_S$ at the rotational angle $\theta$ of the object 103 is given by the Jones vector as in Equation 13:

$$E_S = S_{rot} \times E_0 \tag{13}$$

The beam splitter means 105 splits the light $L_s$ that has birefringence information of the object 103 into beams $L_1$ and $L_2$ while maintaining the polarization of the light $L_s$. The polarizations of the beams $L_1$ and $L_2$ are expressed by Equations 14 and 15 using the Jones vectors where $r_s$, $r_p$, $t_p$ and $t_s$ are complex amplitude reflectance and complex amplitude transmittance to p-polarized light and s-polarized light of the parallel plate in the beam splitter means 105, which have been calculated or measured in advance for corrective operation in the operation part 110:

$$E_{S1} = r_s r_p E_S \tag{14}$$

$$E_{S2} = t_s t_p E_S \tag{15}$$

The beam $L_1$ is incident upon the light-quantity detector means 107 through the polarization element 106 that is oriented relative to the polarization element 102 so that the polarization direction is in parallel nicols. The beam $L_2$ is incident upon the light-quantity detector means 109 through the polarization element 108 that is oriented relative to the polarization element 102 so that the polarization direction is in crossed nicols. The Jones matrixes of the polarization elements 106 and 108 are expressed as in Equations 16 and 17:

$$A_H = \begin{pmatrix} 1 & 0 \\ 0 & 0 \end{pmatrix} \tag{16}$$

$$A_V = \begin{pmatrix} 0 & 0 \\ 0 & 1 \end{pmatrix} \tag{17}$$

The beams $L_1$ and $L_2$ received by the light-quantity detector means 107 and 109 are expressed as in Equations 18 and 19 using the Jones vectors:

$$E_1 = A_H \times E_{S1} \tag{18}$$

$$E_2 = A_V \times E_{S2} \tag{19}$$

The light-quantity detector means 107 and 109 detect light signals of the beams $L_1$ and $L_2$, and output detection signals corresponding to their light intensities to the operation part 110 on a real-time basis for corrective operations. The light intensities detected by the light-quantity detector means 107 and 109 after the corrections are expressed as in Equations 20 and 21 where a suffix * means a complex conjugate relationship:

$$I_1 = (E_1^* \cdot E_1)/|r_s r_p|^2 \tag{20}$$

$$I_2 = (E_2^* \cdot E_2)/|t_s t_p|^2 \tag{21}$$

The light intensities $I_1$ and $I_2$ received by the light-quantity detector means 107 and 109 vary like a sine curve with rotational angle $\theta$ of the object 103. The intensity ratio $I_2/I_1$ between the light intensities $I_1$ and $I_2$ to rotational angle $\theta$ of the object 103 may monitor a variance curve representative of ellipticity of birefringence ellipsoid that indicates birefringence information of the object 103.

Figure 3:
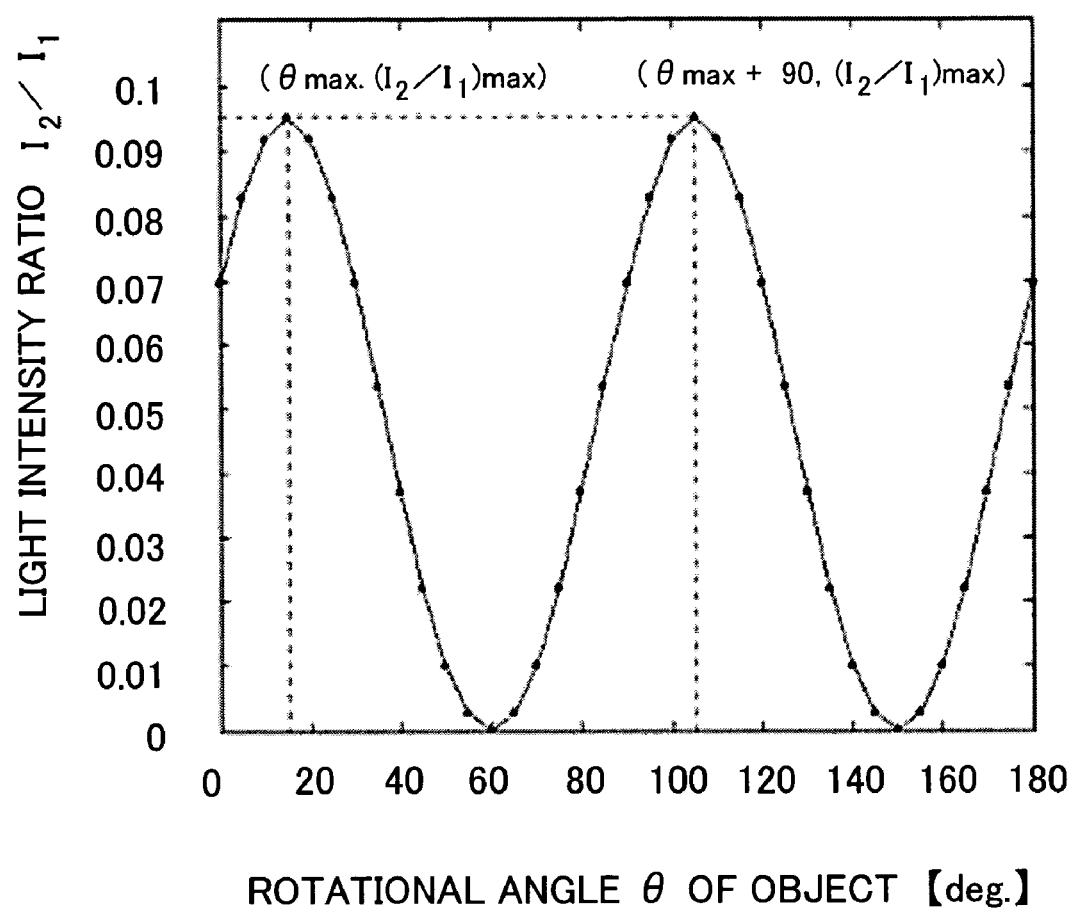
FIG. 3 is an output example of the first embodiment.

FIG. 3 shows an output example of the intensity ratio $I_2/I_1$ to rotational angle $\theta$ of the object 103. In FIG. 3, the maximum intensity ratio $I_2/I_1$ provides a relative angle of 45° between the polarization direction of the polarization element 102 and the azimuth of a principal axis of the object 103, and the exit light $L_s$ of the object 103 provides the maximum ellipse polarized light. The intensity ratio $I_2/I_1$ indicates the ellipticity of the ellipse polarized light, and the phase difference $\Delta$ [deg.] and the azimuth of a principal axis $\Phi$ [deg.] of the object 103 and the Jones matrix of the object 103 are expressed as in Equations 22 and 23 where $(I_2/I_1)$ max and $\theta$max are maximum values of the intensity ratio $I_2/I_1$ of the variance curve:

$$\Delta = 2\arctan(\sqrt{(I_2/I_1)_{max}}) \tag{22}$$

$$\Phi = \pm 45 - \theta_{max} \tag{23}$$

The retardation magnitude [nm/cm] of the object 103 is expressed as in Equation 24 where $\lambda$ [nm] is a wavelength of a light source and d [cm] is a thickness of the object:

$$Re = \Delta\lambda/360d \tag{24}$$

The birefringence measurement apparatus of the instant embodiment is suitable for measurements using ultraviolet as a light source since a measurement optical system does not require a phase plate, such as a quarter-wave plate.

In addition, the birefringence measurement apparatus of the instant embodiment has only one optical element that is to be rotationally driven, and thus provides accurate birefringence measurements since it is not necessary to synchronize rotational driving periods of two optical elements as in the conventional measurement method.

The birefringence measurement apparatus of the instant embodiment uses the beam splitter means that splits light while maintaining its polarization, and detect birefringence information of the target light with two light-receiving elements, thereby simultaneously measuring the maximum and minimum light quantities of the ellipse without being affected by the light quantity variances of the light source, and providing accurate birefringence measurements.

The birefringence measurement apparatus of the instant embodiment detects the light quantity to a rotation of the object 103, and measures the retardation magnitude and the azimuth of the principal axis of the object 103 at the same time within shorter measurement time than the conventional measurement method.

The birefringence measurement apparatus of the instant embodiment may cancel out the influence of manufacture errors, etc. of the optical elements by averaging plural pieces of birefringence data operated at an interval of 90° as the object 103 rotates. The information of the operation part 110 is fed back to the controller 111 and the sampling number of a rotational angle range and measurement data is controlled for locally precise measurements according to the retardation magnitude of the object 103.

Embodiment 2

Figure 4:
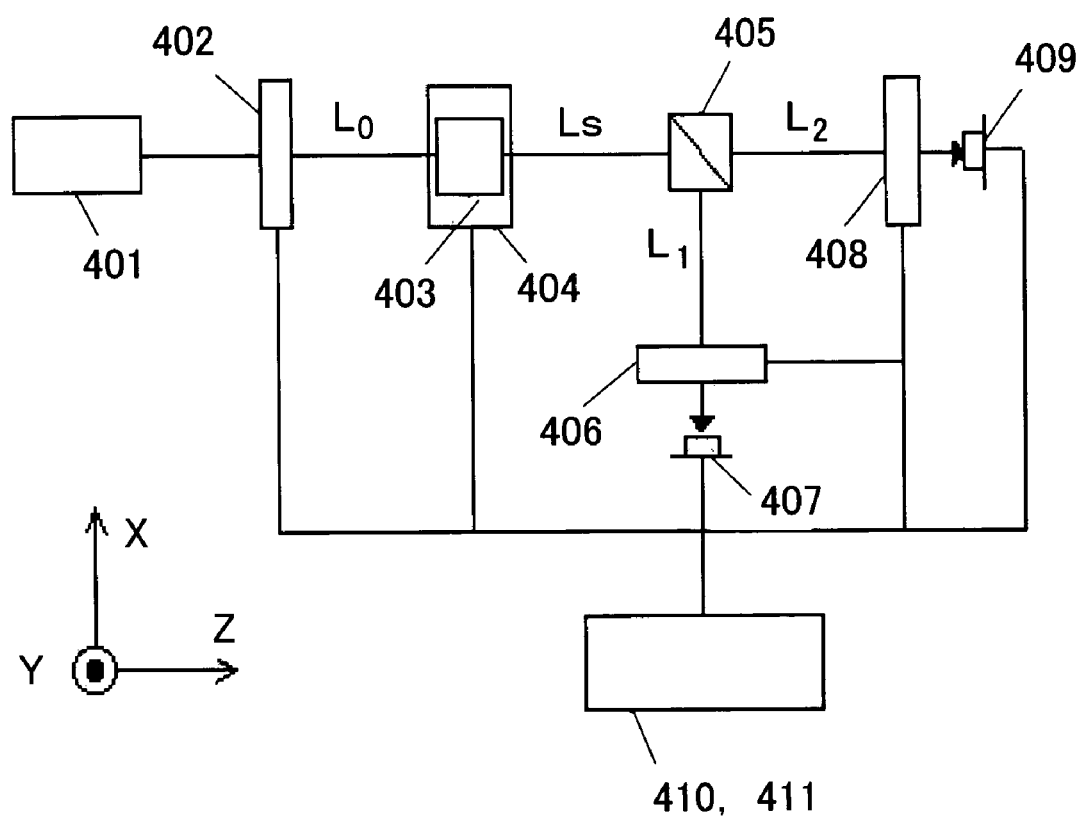
FIG. 4 is a view of a birefringence measurement apparatus of a second embodiment.

FIG. 4 is a schematic view of a birefringence measurement apparatus of a second embodiment according to the present invention. A description will be given of the birefringence measurement apparatus of the second embodiment with reference to FIG. 4.

The instant embodiment uses similar structure to that of the first embodiment except that the instant embodiment is configured to use rotational control means for the polarization elements 102, 106, and 108. A detailed description of the common structure will be omitted by assigning corresponding reference numerals to the last two digits, and different portion from the first embodiment will be mainly discussed.

In FIG. 4, the birefringence measurement apparatus of the second embodiment includes a light source 401, a polarization element 402, an object to be measured 403, a sample stage 404, beam splitter means 405, polarization elements 406 and 408, light-quantity detector means 407 and 409, an operation part 410, and a controller 411.

The light emitted from the light source 401 is incident upon the object 403 after converted into a linearly polarized light $L_0$ via the polarization element 402 whose rotation around the optical axis is controlled by the controller 411.

The polarization element 402 has a rotary mechanism, a rotation of which is controlled by a stepping motor, etc. The stepping motor is controlled based on a command of the controller 411, and one cycle of birefringence measurement is a rotation from 0° to 180° (or 0° to 360°) in the azimuth of the fast axis relative to the baseline axis.

The sample stage 404 has a measurement position varying mechanism, such as an XY stage, which may variably control a measurement position manually or automatically on a surface orthogonal to the optical-axis direction. In other words, the sample stage 404 may measure the two-dimensional birefringence distribution on the measurement surface.

The light Ls that has birefringence information of the object 403 is split by the beam splitter means 405 into beams $L_1$ and $L_2$ while the polarization of the light Ls is maintained.

The beam $L_1$ is incident upon the light-quantity detector means 407 through the polarization element 406 that is rotationally controlled relative to the polarization element 402 so that the polarization direction is in parallel nicols.

The beam $L_2$ is incident upon the light-quantity detector means 409 through the polarization element 408 that is rotationally controlled relative to the polarization element 402 so that the polarization direction is in crossed nicols.

The light-quantity detector means 407 and 409 detect these light signals which include the birefringence information of the object 403, i.e., a retardation magnitude and an azimuth of a principal axis, and output detection signals corresponding to the light intensities of these light signals to the operation part 410 on a real-time basis.

The operation part 410 and controller 411 store a CPU and a memory, and control actions of each component in the birefringence measurement apparatus, such as the light source 401, polarization elements 402, 406 and 408 and sample stage 404. By executing a preset operational algorithm based on the detection signals detected by the light-quantity detector means 407 and 409, a phase difference Δ and an azimuth of fast axis Φ are operated and the operational result of the birefringence measurement is output to an output unit (not shown).

A description will be given of the birefringence measurement method of the second embodiment according to the present invention. The polarization of the light emitted from the light source 401 is expressed as in Equation 25 where δ is a phase difference in the orthogonal component of the exit light.

$$E_o = \begin{pmatrix} 1 \\ e^{-i\delta} \end{pmatrix} \quad (25)$$

The exit light from the light source 401 is converted into the linear polarized light via the polarization element 402, a rotation of which around the optical axis is controlled the controller 411. The Jones matrix of the rotationally controlled polarization element 402 is expressed as in Equation 26 using the polarization elements 402 and the Jones matrixes in Equations 8 and 11 where θ is a rotational angle of the polarization element 402 to the baseline axis:

$$P_{Hrot} = R_\theta \times P_H \times R_{-\theta} \quad (26)$$

The exit beam $L_o$ from the polarization element 402 transmits through the object 403, and is converted into elliptically polarized light that occurs due to a phase offset resulting from a difference of refractive index of two principal axes of the object 403, i.e., a fast axis and a slow axis. The polarization of the exit beam $L_s$ from the object 403 at a rotational angle θ of the polarization element 402 is expressed as in Equation 27 using the Jones matrix:

$$E_S = S \times P_{Hrot} \times E_0 \quad (27)$$

The beam splitter means 405 splits the light $L_s$ that has birefringence information of the object 403 into beams $L_1$ and $L_2$ while maintaining the polarization of the light $L_s$. The polarizations of the beams $L_1$ and $L_2$ are expressed by the above Equations 14 and 15 using the Jones vectors where $r_s$, $r_p$, $t_p$ and $t_s$ are complex amplitude reflectance and complex amplitude transmittance to p-polarized light and s-polarized light of the parallel plate in the beam splitter means 405, which have been calculated or measured in advance for corrective operation in the operation part 410:

$$E_{S1} = r_s r_p E_S \quad (14)$$

$$E_{S2} = t_s t_p E_S \quad (15)$$

The polarization element 406 is rotationally controlled by the controller 411 relative to the polarization element 402 so that the polarization direction is in parallel nicols. The polarization element 408 that is rotationally controlled by the controller 411 relative to the polarization element 402 so that the polarization direction is in crossed nicols. The polarizations of the beams $L_1$ and $L_2$ received by the light-quantity detector means 407 and 409 are expressed as in Equations 28 and 29:

$$E_1 = R_\theta \times A_H \times R_{-\theta} \times E_{S1} \quad (28)$$

$$E_2 = R_\theta \times A_V \times R_{-\theta} \times E_{S2} \quad (29)$$

The light-quantity detector means 407 and 409 detect light signals of the beams $L_1$ and $L_2$, and output detection signals corresponding to their light intensities to the operation part 410 on a real-time basis for corrective operations.

The same algorism as that of the first embodiment is used to calculate the retardation magnitude and the azimuth of a principal axis of the object 403 using detection signals detected by the light-quantity detector means 407 and 409, and a description thereof will be omitted.

The birefringence measurement apparatus of the instant embodiment uses a non-rotatable object 403, and is applicable to a large aperture sample whereas the structure of the first embodiment has a difficulty in handling such an object.

The birefringence measurement apparatus of the instant embodiment is suitable for measurements using ultraviolet as a light source since a measurement optical system does not require a phase plate, such as a quarter-wave plate.

The birefringence measurement apparatus of the instant embodiment uses the beam splitter means that splits light while maintaining its polarization, and detect birefringence information of the target light with two light-receiving elements, thereby simultaneously measuring the maximum and minimum light quantities of the ellipse without being affected by the light quantity variances of the light source, and providing accurate birefringence measurements.

The birefringence measurement apparatus of the instant embodiment detects the light quantity to rotations of the polarization elements 402, 406 and 408, and measures the retardation magnitude and the azimuth of the principal axis of the object 403 at the same time within shorter measurement time than the conventional measurement method.

The birefringence measurement apparatus of the instant embodiment may cancel out the influence of manufacture errors, etc. of the optical elements by averaging plural pieces of birefringence data operated at an interval of 90° as the polarization elements 402, 406 and 408 rotate. The information of the operation part 410 is fed back to the controller 111 and the sampling number of a rotational angle range and measurement data is controlled for locally precise measurements according to the retardation magnitude of the object 403.

The instant embodiment may arrange a polarization element (not shown) between the light source 401 and the polarization element 402, which converts polarization of the incident light into linear polarized light.

Third Embodiment

Figure 5:
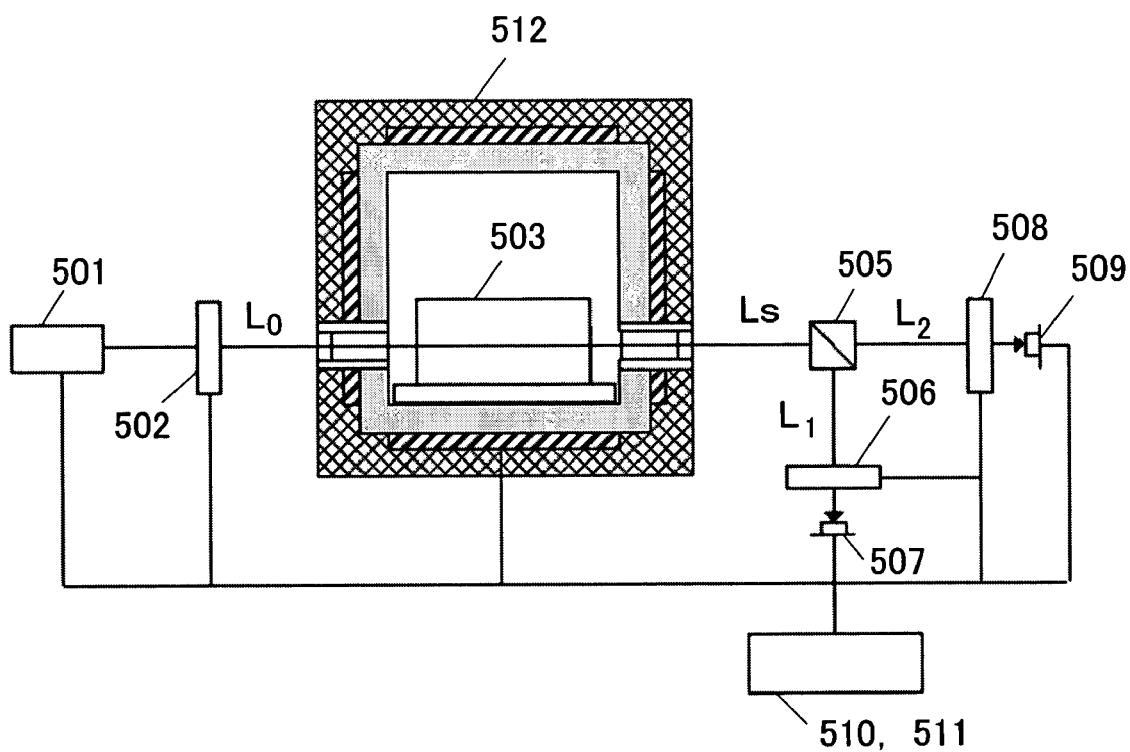
FIG. 5 is a strain remover of a third embodiment.
Figure 6:
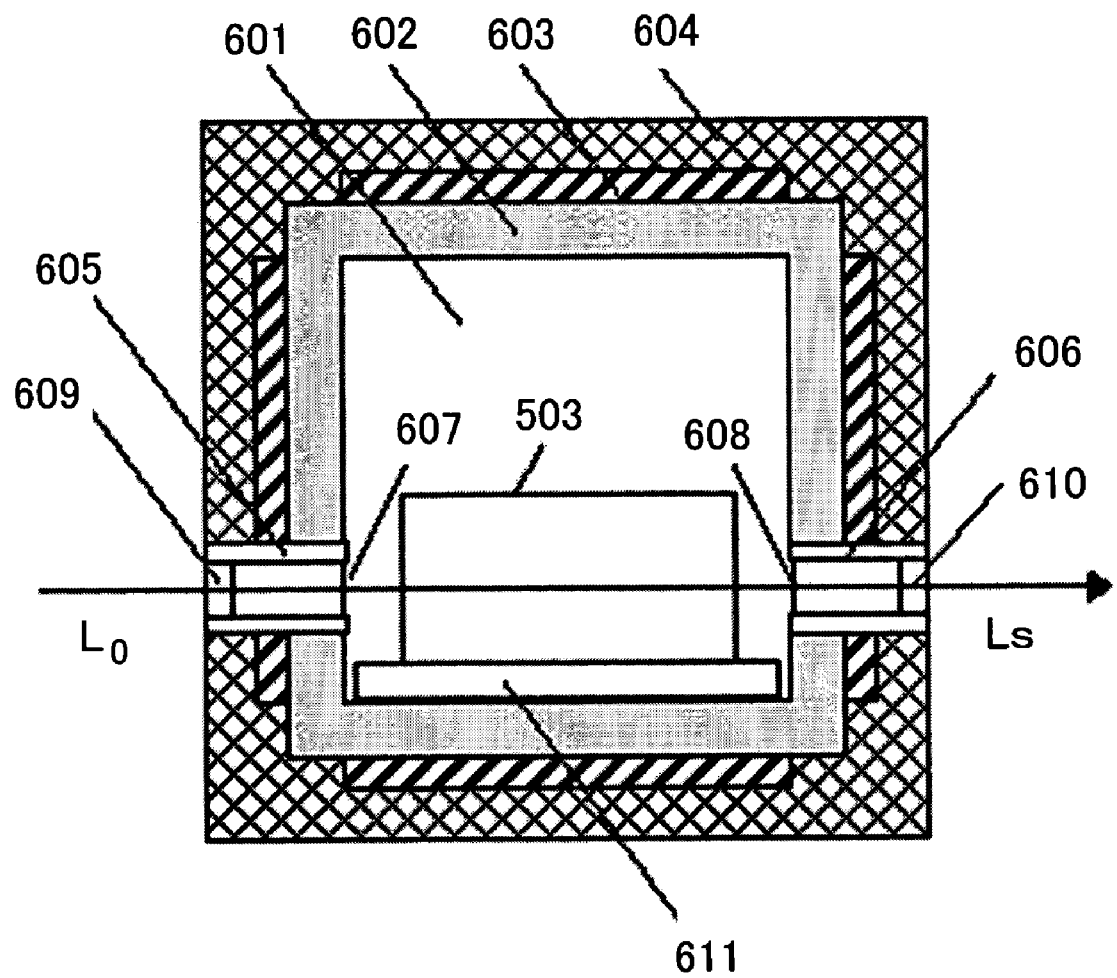
FIG. 6 is a view of a heat treatment part of the third embodiment.

FIGS. 5 and 6 are schematic views of a strain remover of a third embodiment according to the present invention. A description will be given of the strain remover of the third embodiment with reference to FIGS. 5 and 6.

The instant embodiment uses similar structure to the birefringence measurement apparatus of the second embodiment except that the instant embodiment is configured to store an object to be measured 404 in a heat treatment part. A detailed description of the common structure will be omitted by assigning corresponding reference numerals to the last two digits, and different portion from the second embodiment will be mainly discussed.

In FIG. 5, the strain remover of the third embodiment includes a light source 501, a polarization element 502, an object to be measured 503, a heat treatment part 504, a beam splitter means 505, polarization elements 506 and 508, light-quantity detector means 507 and 509, an operation part 510, and a controller 511.

The strain remover of the third embodiment is configured to execute a heat treatment to the object 503 by storing the object 503 in the heat treatment part 512, measuring birefringence changes of the object 503 with time in the heat treatment step, and enabling the controller 511 to control heat treatment conditions based on the measurement result so that the retardation magnitude of the object 503 may be within the predetermined range.

A description will be given of the heat treatment part 512 with reference to FIG. 6.

The heat treatment part 512 includes a stainless container 602 having a sample storage chamber 601, plural heating units 603 each of which has an independently temperature controllable heater on side, bottom, and upper parts of the stainless container 602, and an adiabatic wall 604.

The temperature in the sample storage chamber 601 is controllable by a temperature controller. The object 503 housed in the container may be uniformly heat-treated by heating the independently temperature controllable heating units 603 installed at four sides of the stainless container 602, and reducing temperature non-uniformity in the sample storage chamber 601.

The heat treatment part 512 is provided with a light guide tube 605 for introducing light $L_o$ emitted from the light source 501 into the sample storage chamber 601, and a light guide tube 606 for introducing transmitting light $L_s$ of the object 503 to the outside the sample storage chamber 601. The light guide tubes 605 and 606 are provided with transparent shutters 607, 608 for shielding the atmosphere in the sample storage chamber 601 from the outside, transparent quartz window or calcium-fluoride window 609, 610, etc.

The object 503 is optically polished so as to have parallel incident and exit surfaces of the laser light, and held on the sample holder rack 611 so that the laser beam perpendicularly enters and exits the incident and exit surfaces.

The strain remover of the instant embodiment may measure the retardation magnitude changes of the object 503 with time in the heat treatment step on a real-time basis, and enables the controller 511 to feedback-control, based on the measurement result, the heat treatment conditions of the object 503, such as temperature, holding time, temperature rise speed, and cooling speed, thereby shortening the retardation magnitude control and heat treatment time of the object 503.

The instant embodiment may arrange a polarization element (not shown) between the light source 501 and the polarization element 502, which converts polarization of the incident light into linear polarized light.

Fourth Embodiment

Figure 7:
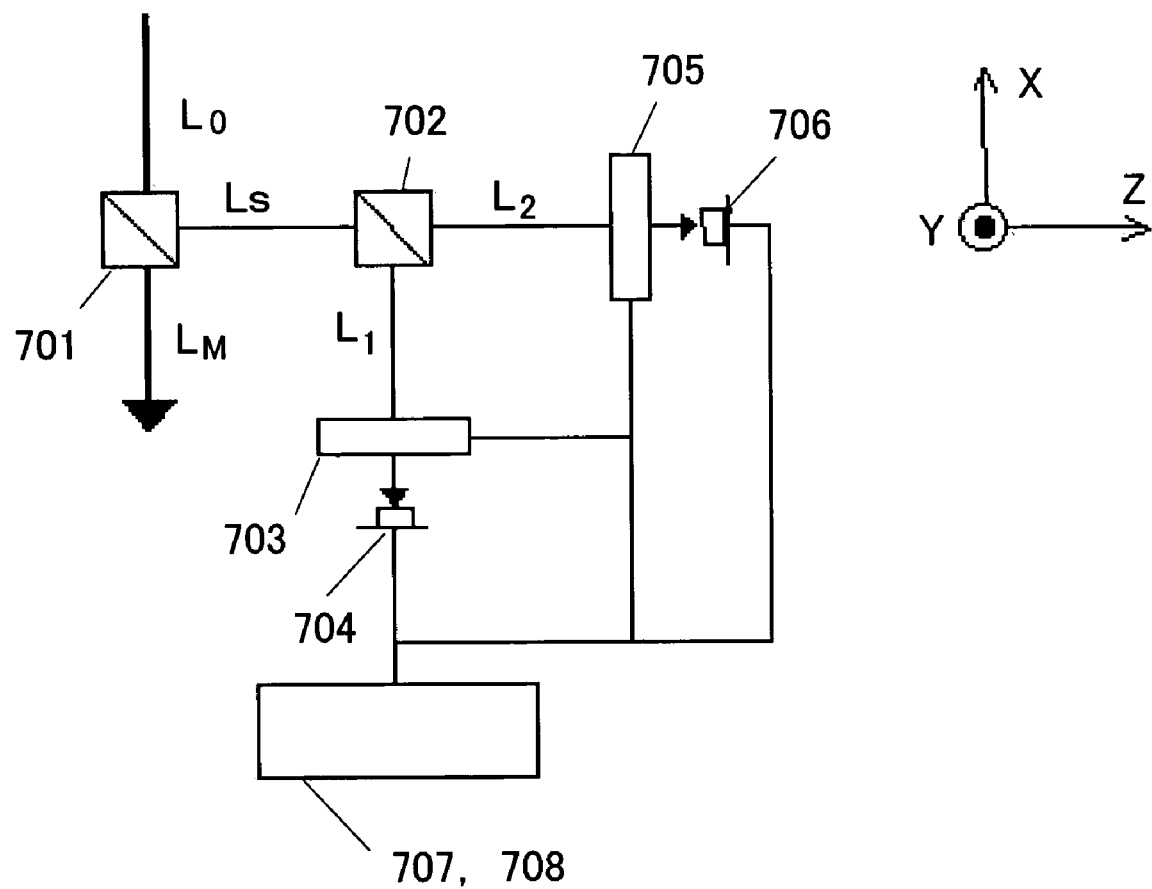
FIG. 7 is a view of a polarimeter of a fourth embodiment.

FIG. 7 is a schematic view of a polarimeter of a fourth embodiment according to the present invention. A description will be given of the polarimeter of the fourth embodiment with reference to FIG. 7.

In FIG. 7, the polarimeter of the fourth embodiment includes beam splitter means 701, 702, polarization elements 703, 705, light-quantity detector means 704, 706, operation part 707, and a controller 708.

The beam splitter means 701 splits light $L_o$ emitted from a desired light source unit, into beams $L_M$ and $L_S$ having the same polarization as the light $L_o$. The polarimeter of the fourth embodiment uses the light $L_S$ to detect polarization. The light $L_M$ is introduced into a desired unit.

The beam $L_S$ that has been split by the beam splitter means 701 is split by the beam split means 702 into beams $L_1$ and $L_2$ having the same polarization. These beams $L_1$ and $L_2$ are incident upon the light-quantity detector means 704 and 706 via the polarization elements 703 and 705 that are rotationally controlled by the controller 708 around the optical axis. The polarization elements 703 and 705 are oriented so that they are in crossed nicols.

The light-quantity detector means 704 and 706 detect these light signals which include the birefringence information of the beam to be measured, and output detection signals corresponding to the light intensities of the light signal to the operation part 707 on a real-time basis.

A description will be given of a polarization detecting method of the fourth embodiment according to the present invention with reference to FIG. 7.

The polarization of the beam $L_S$ to be measured that has a proceeding direction as a Z-axis is expressed as in Equation 32 by dissolving the electric field vector into orthogonal two components where $A_X$ and $A_Y$ are amplitudes of each component, and $\delta$ is a phase difference between the X and Y components:

$$E_S = \begin{pmatrix} A_x \\ A_y \exp(i\delta) \end{pmatrix} \quad (30)$$

The beam splitter means 105 splits the light $L_s$ into the beams $L_1$ and $L_2$ while maintaining the polarization of the light $L_s$. The polarizations of the beams $L_1$ and $L_2$ are expressed by the above Equations 14 and 15 using the Jones vectors where $r_s$, $r_p$, $t_p$ and $t_s$ are complex amplitude reflectance and complex amplitude transmittance to p-polarized light and s-polarized light of the parallel plate in the beam splitter means 105, which have been calculated or measured in advance for corrective operation in the operation part 707:

$$E_{S1} = r_s r_p E_S \quad (14)$$

$$E_{S2} = t_s t_p E_S \quad (15)$$

The beams $L_1$ and $L_2$ are introduced into the light-quantity detector means 704 and 706 via polarization elements 703 and 705 that are rotationally controlled so that they may maintain a state of crossed nicols. Here, the polarization direction of the polarization element 703 is made to be 0° whereas the polarization direction of the polarization element 705 is made to be 90° for the baseline axis of the rotary surface with θ=0°.

The beams $L_1$ and $L_2$ received by the light-quantity detector means 704 and 706 are expressed as in the above Equations 28 and 29 using the Jones vector:

$$E_1 = R_\theta \times A_H \times R_{-\theta} \times E_{S1} \quad (28)$$

$$E_2 = R_\theta \times A_V \times R_{-\theta} \times E_{S2} \quad (29)$$

The light-quantity detector means 704 and 706 detect light signals of the beams $L_1$ and $L_2$, and output detection signals corresponding to their light intensities to the operation part 707 on a real-time basis for corrective operations. The light intensities detected by the light-quantity detector means 704 and 706 after the corrections are expressed as in the above Equations 20 and 21 where a suffix * means a complex conjugate relationship:

$$I_1 = (E_1^* \cdot E_1)/|r_s r_p|^2 \quad (20)$$

$$I_2 = (E_2^* \cdot E_2)/|t_s t_p|^2 \quad (21)$$

The light intensities $I_1$ and $I_2$ received by the light-quantity detector means 704 and 706 vary like a sine curve with rotational angle θ of the polarization elements 703 and 705. The operation part 707 calculates a intensity ratio $I_2/I_1$ between the light intensities $I_1$ and $I_2$ with rotational angle θ, and converts it into a phase difference Δ using Equation 31 so as to monitor a variance curve representative of polarization information of the beam $L_S$:

$$\Delta = 2 \arctan(\sqrt{(I_2/I_1)}) \quad (31)$$

Figure 8:
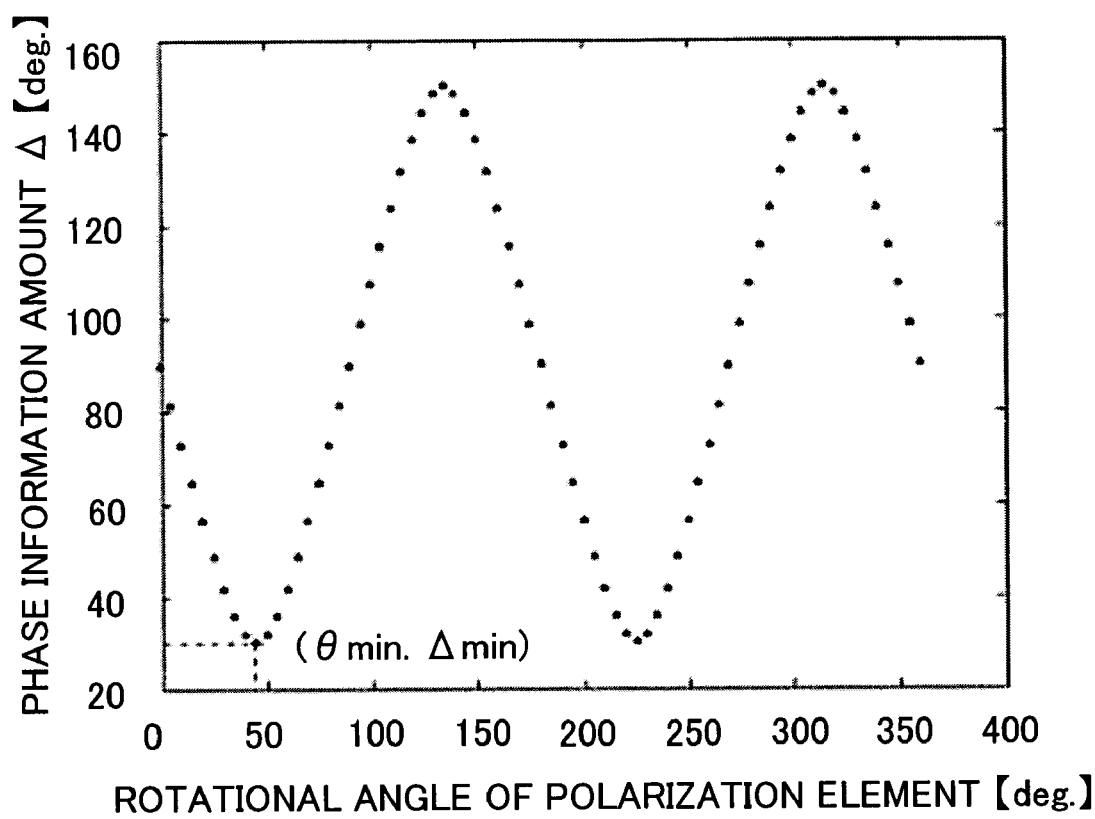
FIG. 8 is an output example of the fourth embodiment.

FIG. 8 shows an output example of the phase difference Δ of the beam $L_S$ with rotational angle θ. A phase difference δ between the X and Y components and an amplitude ratio $A_y/A_x$ of these components may be calculated using Equations 32 and 33 in addition to Δmin that provides the minimum phase difference Δ and the rotational angle θmin at that time in FIG. 8:

$$\delta = \Delta_{min} \quad (32)$$

$$A_y/A_x = \tan(\theta_{min}) \quad (33)$$

The light quantity of the beam $L_S$ is calculated using Equation 34:

$$I = I_1 + I_2 \quad (34)$$

The polarimeter of the instant embodiment may easily measure changes of light-quantity variance with time of the beam to be measured, as well as changes of the polarization with time of the beam to be measured. The polarimeter of the instant embodiment is used for such apparatuses as various types of illumination apparatuses, exposure apparatuses, optical measurement units, optical observation units, and interferometers, in which polarization changes affect performance.

Fifth Embodiment

The exposure apparatus of a fifth embodiment according to the present invention is characterized in having the polarimeter of the fourth embodiment. According to the exposure apparatus of this embodiment, the exposure apparatus may always detect polarization of the illumination system for feedback control so that the illumination system may maintain the polarization always suitable for the exposure. The exposure may detect the accurate exposure dose irrespective of changing polarization performance of the illumination system, and provide an accurate feedback control over the exposure dose.

Sixth Embodiment

The device fabrication method of a sixth embodiment according to the present invention is characterized in using the exposure apparatus of the fifth embodiment. The device fabrication method of this embodiment uses the exposure apparatus to improve throughput as well as providing high-quality devices.

The inventive birefringence measurement apparatus is suitable for measurements using ultraviolet as a light source since it does not require a phaser, such as a quarter-wave plate. Use of the beam splitter means that maintains the polarization may use two or more light receiving elements to detect birefringence information of the beam to be measured for quick and accurate birefringence measurements.

The inventive strain remover measures changes with time of the retardation magnitude of an optical element in the heat treatment step, feedback-controls the heat treatment conditions, and provides control over the retardation magnitude of the optical element and shortened heat treatment time.

The inventive polarimeter may measure changes with time of light amount variance of the beam to be measured, and changes with time of polarization of the beam. The inventive exposure apparatus provides feedback control so that the illumination system may maintain the polarization always suitable for the exposure, and provide accurate feedback control over the exposure dose.

The inventive device fabrication method may not only improve throughput but also provide high-quality devices.

Seventh Embodiment

Figure 9:
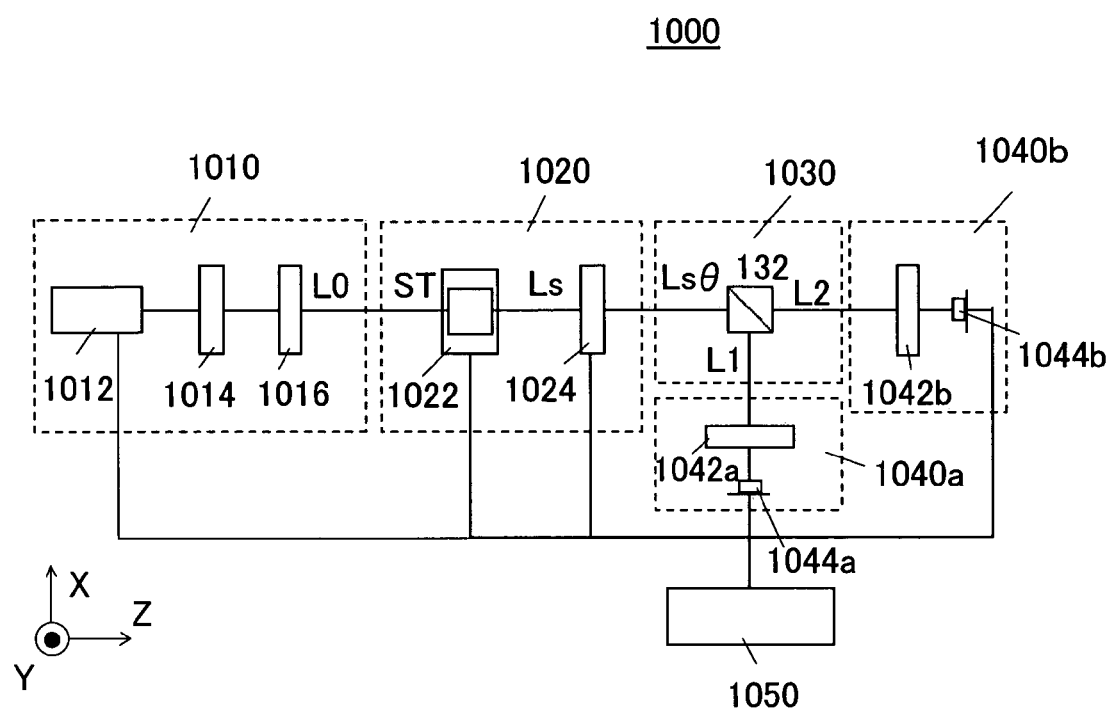
FIG. 9 is a schematic block diagram of a birefringence measurement apparatus of a seventh embodiment according to the present invention.

FIG. 9 is a schematic view of a structure of a birefringence measurement apparatus 1000 of a seventh embodiment according to the present invention. FIG. 9 sets a Z-axis as a proceed direction of light emitted from a light source 1012, an X-axis as a direction perpendicular to the Z-axis on an installation surface of the light source 1012, and a Y-axis as a direction normal to the installation surface of the light source 1012.

The birefringence measurement apparatus 1000 serves to measure birefringence in an object to be measured ST, and includes a light source part 1010, a measurement part 1020, a beam splitter means 1030, detector parts 1040a and 1040b, and a controller 1050.

The light source part 1010 emits light having specific polarization to the object ST, and includes a light source 1012, a linear polarization element 1014, and a quarter-wave plate 1016 in the instant embodiment.

The light source is a light source that emits a predetermined beam to the object ST, and includes a visible-range continuous laser, such as a He—Ne laser. While the birefringence measurement apparatus 1000 of the instant embodiment is suitable for measurements of birefringence of the object ST using the visible-range continuous laser for the light source 1012, the light source 1012 may use any type of light source, such as an ultraviolet pulse laser.

Linear or elliptically polarized light emitted from the light source 1012 is incident upon the object ST after converted into a circularly polarized light $L_O$ via the linear polarization element 1014 that is oriented with a polarization direction at 0° to a baseline axis, e.g., a direction parallel to the installation surface of the light source 1012, preset around the optical axis and on a surface orthogonal to an optical-axis direction, and the quarter-wave plate 1016 that is oriented with an azimuth of a fast axis of 45° to the baseline axis at the exit side of the linear polarization element 1014.

The linear polarization element 1014 may use an optical element that separates orthogonal polarized light components and picks up one linearly polarized light component, such as a Glan-Thompson polarizing prism, a Rochon polarizing prism, a Senarmon polarizing prism, and a Wollaston polarizing prism or a polarization beam splitter made of dielectric multilayer, etc.

The instant embodiment converts light having arbitrary polarization emitted from the light source 1012 into a circularly polarized light using the linear polarization element 1014 and quarter-wave plate 1016, whereby the fast axis direction of the object ST has no dead direction, may output stable polarization and enhance measurement accuracy.

The measurement part 1020 has a stage 1022 that holds the object ST, and a half-wave plate 1024 that has a rotary mechanism.

The stage 1022 has, for example, an XY stage, which may variably control a measurement position of the object ST manually or automatically along orthogonal directions on a surface orthogonal to the optical-axis direction. The stage 1022 varies a measurement range of the object ST, and enables the birefringence to be measured at plural positions. In other words, the stage 1022 controls positions of the object ST, and achieves the two-dimensional birefringence distribution on the measurement surface.

Suppose that the circularly polarized light $L_o$ from the light source part 1010 transmits through the object ST. The circularly polarized light $L_o$ is converted into elliptically polarized light $L_S$ due to a phase difference caused by a refractive index difference between two principal axes of fast and delay axes of the object ST. The elliptically polarized light $L_S$ is incident as a light signal that reflects birefringence information of the phase difference (or retardation magnitude) and azimuth of a principal axis (or azimuth of a principal axis) upon the half-wave plate 1024.

The half-wave plate 1024 has a rotary mechanism, a rotation around the optical axis of which is controlled by a stepping motor (not shown), etc. The stepping motor is controlled based on a command of the controller 1050, which will be described later, and one cycle of birefringence measurement is a rotation from 0° to 180° in the azimuth of a fast axis relative to the baseline axis.

The half-wave plate 1024 serves to covert the rotation around the optical axis while maintaining the polarization of the incident light. In the instant embodiment, when the half-wave plate 1024 rotates by θ, the rotation angle of the elliptically polarized light $L_S$ from the object ST is converted into 2θ while its polarization is maintained, and then the elliptically polarized light $L_S$ enters the beam splitter means 130. In other words, by rotating the half-wave plate 1024, the elliptically polarized light $L_S$ that has birefringence information of the object ST may be converted into beam $L_{S\theta}$ that maintains the polarization of the beam $L_S$.

The beam splitter means 1030 corresponds to the beam splitter means 105 shown in FIG. 2 where the incident light 201 is $L_{S\theta}$, the beams 202, 203, 207 and 208 are $L_1$, $L_2$, $L_1'$ and $L_2'$, respectively in the instant embodiment.

The detectors 1040a and 1040b include linear polarization elements 1042a and 1042b, and light-quantity detector means 1044a and 1044b. The linear polarization elements 1042a and 1042b are arranged so that their polarization directions are 0° to the baseline axis. The first and second beams $L_1$ and $L_2$ are emitted as light signals including the birefringence information representative of the retardation magnitude and azimuth of a principal axis of the object ST to the light-quantity detector means 1044a and 1044b via the linear polarization elements 1042a and 1042b. The light-quantity detector means 1044a and 1044b detect these light signals, and output detection signals corresponding to the light intensities of the light signals to the controller 1050.

The controller 1050 stores a CPU and memory (not shown), and controls actions of each component in the birefringence measurement apparatus 1000, such as the light source 1012, stage 1022, and half-wave plate 1024. By executing a preset operational algorithm based on the detection signals detected by the light-quantity detector means 1044a and 1044b, the controller 1050 calculates a phase difference and an azimuth of a slow axis of the object ST. The controller 1050 may output the calculation result of the birefringence measurement to an output unit (not shown).

A description will be given of a birefringence measuring method using the birefringence measurement apparatus 1000. The light source part 1010 converts the linearly or elliptically polarized light emitted from the light source 1012 into horizontally linearly polarized light $E_O$ via the linear polarization element 1014 that is oriented with a polarization direction at 0° to a baseline axis. The polarization of the horizontally linearly polarized light $E_O$ is expressed using the Jones matrix as in Equation 9:

$$E_o = \begin{pmatrix} 1 \\ 0 \end{pmatrix} \tag{9}$$

The horizontally linearly polarized light $E_O$ is incident upon the object ST after converted into circularly polarized light $L_O$ via the quarter-wave plate 116 that is oriented with an azimuth of slow axis of 45° relative to the baseline axis at the exit side of the linear polarization element 1014. The Jones matrix Q of the quarter-wave plate 1016 is expressed as in Equation 35:

$$Q = \begin{pmatrix} \exp(i*\pi/4) & 0 \\ 0 & \exp(-i*\pi/4) \end{pmatrix} \quad (35)$$

The Jones matrix $R_{\pi/4}$ that converts a rotation of the quarter-wave plate 1016 to such a position that the polarization direction becomes 45° to the baseline axis is expressed as in Equation 36:

$$R_{\pi/4} = \begin{pmatrix} \cos(\pi/4) & -\sin(\pi/4) \\ \sin(\pi/4) & \cos(\pi/4) \end{pmatrix} \quad (36)$$

The circularly polarized light $L_O$ is expressed using the Jones matrix as in Equation 37:

$$L_O = R_{\pi/4} \times Q \times R_{-\pi/4} \times E_0 \quad (37)$$

The circularly polarized light $L_O$ transmits through the object ST, and is converted into elliptically polarized light $L_S$ due to phase offset resulting from a difference of refractive index of two principal axes of the object ST, i.e., a fast axis and a slow axis.

The phase difference $\Delta$ and the azimuth of a principal axis $\Phi$ of the object ST and the Jones matrix S of the object ST are expressed as in Equation 10:

$$S = \begin{pmatrix} \cos(\phi) & -\sin(\phi) \\ \sin(\phi) & \cos(\phi) \end{pmatrix} \quad (10)$$

$$\begin{pmatrix} \exp(i*\Delta/2) & 0 \\ 0 & \exp(-i*\Delta/2) \end{pmatrix} \begin{pmatrix} \cos(\phi) & \sin(\phi) \\ -\sin(\phi) & \cos(\phi) \end{pmatrix}$$

The polarization of the elliptically polarized light $L_S$ is expressed as in Equation 38 using the Jones vector S:

$$L_S = S \times L_O \quad (38)$$

The elliptically polarized light $L_S$ having the birefringence information of the object ST enters the half-wave plate 1024, and rotated while its polarization is maintained, when the half-wave plate 1024 is rotated. The Jones matrix H of the half-wave plate 1024 is expressed as in Equation 39:

$$H = \begin{pmatrix} \exp(i*\pi/2) & 0 \\ 0 & \exp(-i*\pi/2) \end{pmatrix} \quad (39)$$

As the half-wave plate 1024 is rotationally driven around the optical axis by the controller 1050, the Jones matrix $R_\theta$ of the rotational conversion is expressed as in Equation 11 where $\theta$ is a rotational angle from an origin that is a position where the azimuth of a fast axis is 0° relative to the baseline axis:

$$R_\theta = \begin{pmatrix} \cos(\theta) & -\sin(\theta) \\ \sin(\theta) & \cos(\theta) \end{pmatrix} \quad (11)$$

The half-wave plate 1024 rotationally converts the elliptically polarized light $L_S$ having the birefringence information into the beam $L_{S\theta}$ while maintaining the polarization, and the polarization of the beam $L_{S\theta}$ is expressed as in Equation 40 using the Jones vector:

$$L_{S\theta} = R_\theta \times H \times R_{-\theta} \times L_S \quad (40)$$

The beam splitter part 1032 in the beam splitter means 1030 splits the light $L_{S\theta}$ having the birefringence information of the object ST into the first and second beams $L_1$ and $L_2$ while maintaining the polarization of the light $L_{S\theta}$. The first and second beams $L_1$ and $L_2$ are emitted to the light-quantity detector means 1044a and 1044b via the linear polarization element 1042a that is oriented with its polarization direction at 0° relative to the baseline axis, and the linear polarization element 1042b that is oriented with its polarization direction at 90° relative to the baseline axis.

The Jones vector $A_H$ of the linear polarization element 1042a and the Jones vector $A_v$ of the linear polarization element 1042b are expressed as in the above Equations 16 and 17:

$$A_H = \begin{pmatrix} 1 & 0 \\ 0 & 0 \end{pmatrix} \quad (16)$$

$$A_V = \begin{pmatrix} 0 & 0 \\ 0 & 1 \end{pmatrix} \quad (17)$$

The polarizations of the first and second beams $L_1$ and $L_2$ received by the light-quantity detector means 1044a and 1044b are expressed as in Equations 41 and 42 using the Jones vectors:

$$E_1 = A_H \times L_S \quad (41)$$

$$E_2 = A_V \times L_S \quad (42)$$

The light-quantity detector means 1044a and 1044b detect light signals of the beams $L_1$ and $L_2$, and output detection signals corresponding to their light intensities to the operation part 1050. The light intensities $I_1$ and $I_2$ received by the light-quantity detector means 1044a and 1044b are expressed as in Equations 43 and 44 where $r_s$, $r_p$, $t_p$ and $t_s$ are complex amplitude reflectance and complex amplitude transmittance to p-polarized light and s-polarized light of the parallel plate in the beam splitter means 1030, which have been calculated or measured in advance and a suffix * means a complex conjugate relationship:

$$I_1 = r_p^2 r_s^2 (E_1^* \cdot E_1) \quad (43)$$

$$I_2 = t_p^2 t_s^2 (E_2^* \cdot E_2) \quad (44)$$

The light intensities $I_1$ and $I_2$ received by the light-quantity detector means 1044a and 1044b vary like a sine curve with rotational angle $\theta$ of the half-wave plate 1024. The sine variance curve due to the birefringence is calculated based on changing light intensities $I_1$ and $I_2$, and the retardation magnitude and azimuth of a fast axis of the object ST are calculated from the amplitude and phase of the sine variance curve.

Figure 10:
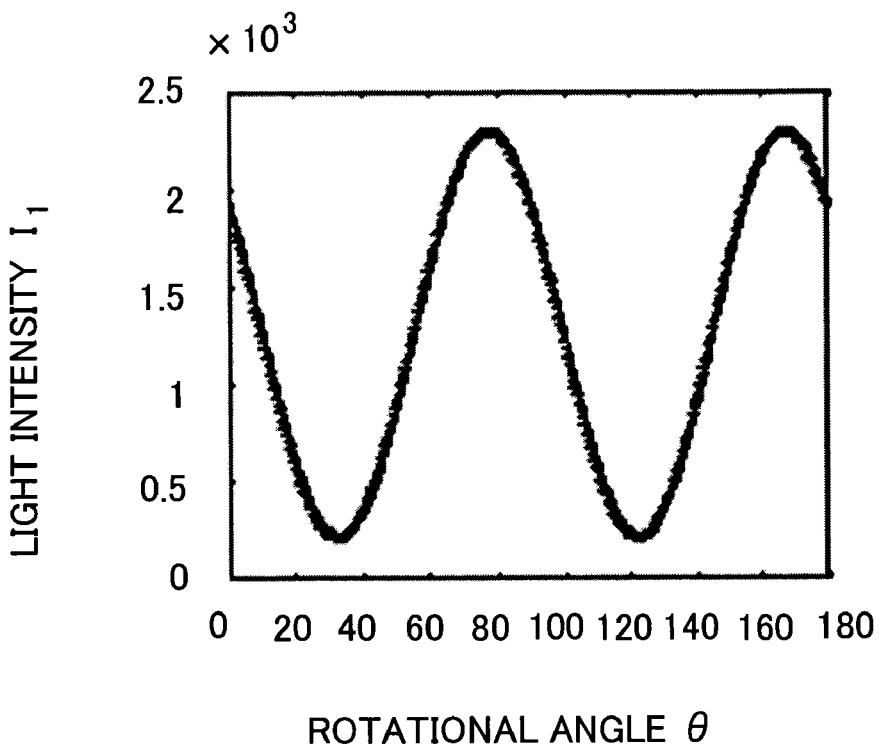
FIG. 10 is an exemplary graph a curve that changes like a sine curve of a light intensity $I_1$ to a rotational angle of a half-wave plate.
Figure 11:
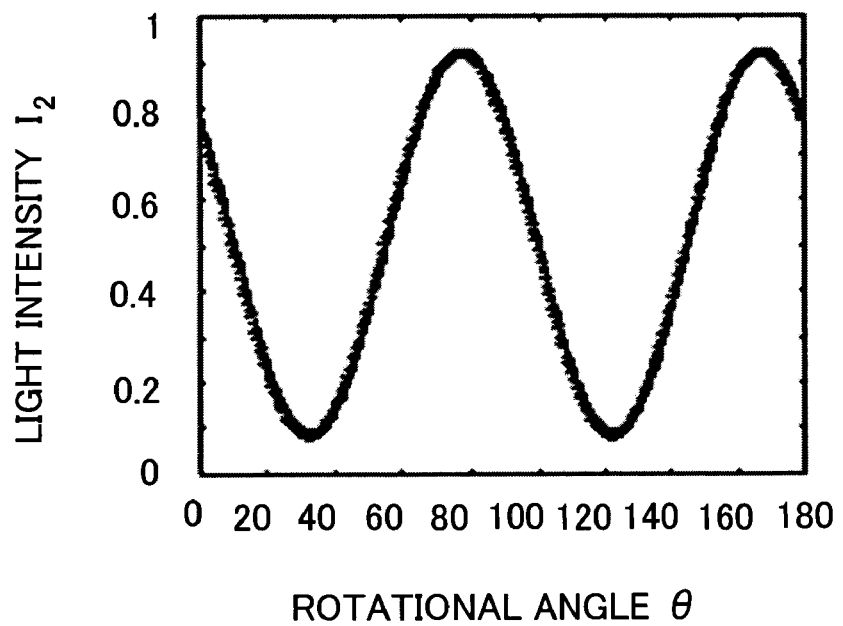
FIG. 11 is an exemplary graph a curve that changes like a sine curve of a light intensity $I_2$ to a rotational angle of a half-wave plate.

FIGS. 10 and 11 show graphs of exemplary sine variance curves of the light intensities $I_1$ and $I_2$ relative to the rotational angle $\theta$ of the half-wave plate 1024. FIGS. 10 and 11 set the light intensities $I_1$ and $I_2$ along the ordinate axis, and the rotational angle $\theta$ of the half-wave plate 1024 along the abscissa axis. Referring to FIGS. 10 and 11, the phase difference $\Delta$ of the object ST is calculated by Equation 45 using a ratio between the maximum and minimum values $I_{max}$ or $I_{min}$ of the light intensity $I_1$ or $I_2$:

$$\Delta = 90 - 2\tan^{-1}(\sqrt{I_{min}/I_{max}}) \quad (45)$$

The azimuth Φ of a fast axis is calculated using Equation 46 where $\theta_1$ is a rotational angle of the half-wave plate 1024 when the light intensity $I_1$ initially exhibits the minimum value $I_{min}$ or the light intensity $I_2$ initially exhibits the maximum value $I_{max}$, and $\theta_2$ is a rotational angle of the half-wave plate 1024 when the light intensity $I_1$ initially exhibits the maximum value $I_{max}$ or the light intensity $I_2$ initially exhibits the minimum value $I_{min}$:

$$\Phi = 2\theta_1 - 45 = 2\theta_2 - 135 \tag{46}$$

The birefringence measurement apparatus 1000 uses the half-quarter plate 1024 as an optical element that is rotationally driven, and does not have to synchronize rotationally drive periods of two optical elements, for example, as in the conventional heterodyne method, thereby achieving precise birefringence measurement without influence of measurement errors, such as a synchronous offset. The beam splitter means 1030 that maintains the polarization of the elliptically polarized light including the birefringence information of the object ST and two or more light-quantity detector means detect the light quantity for precise birefringence measurements.

Eighth Embodiment

Figure 12:
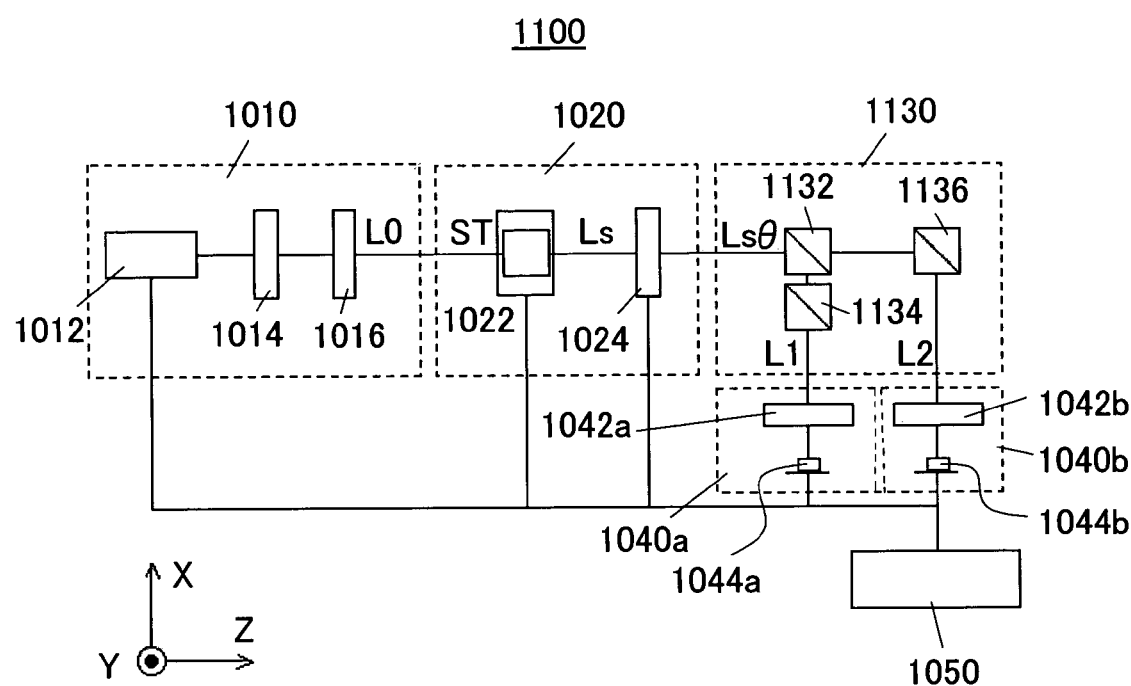
FIG. 12 is a schematic block diagram of a birefringence measurement apparatus of an eighth embodiment according to the present invention.

A description will be given of a birefringence measurement apparatus 1100 of an eighth embodiment according to the present invention. FIG. 12 is a schematic block diagram of the birefringence apparatus 1100. The birefringence apparatus 1100 has the same structure as that of the birefringence apparatus 1000 except that the birefringence apparatus 1100 has a beam splitter means 1130 that includes three beam splitter parts 1132, 1134 and 1136 different from the beam splitter means 1030.

The beam splitter parts 1132, 1134 and 1136, each including three parallel plates, serve to split the incident light into reflection and transmission beams while maintaining the polarization of the incident light. The beam splitter means 1130 is characterized in that it splits the light $L_{S\theta}$ having the birefringence information of the object ST into the first (reflection) light $L_1$ and second (transmission) light $L_2$ while maintaining, and equalizes the light quantities between the first light $L_1$ and second light $L_2$.

The first light $L_1$ reflects twice on the parallel plates of the beam splitter parts 1132 and 1134, transmits twice the parallel plates of the beam splitter parts 1132 and 1134 and is rotationally converted by 90° while maintains the polarization of the light $L_{S\theta}$, and enters the detector part 1040a. The second light $L_2$ reflects twice on the parallel plates of the beam splitter parts 1132 and 1136, transmits twice the parallel plates of the beam splitter parts 1132 and 1136 and is rotationally converted by 90° while maintains the polarization of the light $L_{S\theta}$, and enters the detector part 1040b. The beam splitter part 1134 uses only transmission beams among split beams for correction means for equalizing the first and second beams $L_1$ and $L_2$.

The detectors 1040a and 1040b include linear polarization elements 1042a and 1042b, and light-quantity detector means 1044a and 1044b. The linear polarization elements 1042a and 1042b are arranged so that their polarization directions are 0° to the baseline axis. The first and second beams $L_1$ and $L_2$ are emitted as light signals including the birefringence information representative of the retardation magnitude and azimuth of a principal axis of the object ST to the light-quantity detector means 1044a and 1044b via the linear polarization elements 1042a and 1042b.

The polarizations of the first and second beams $L_1$ and $L_2$ received by the light-quantity detector means 1044a and 1044b are expressed as in Equations 47 and 48 using the Jones vectors:

$$L_1 = A_H \times Ls \tag{47}$$

$$L_2 = A_V \times Ls \tag{48}$$

The light-quantity detector means 1044a and 1044b detect these light signals, and output detection signals corresponding to their light intensities to the operation part 1050. The light intensities $I_1$ and $I_2$ received by the light-quantity detector means 1044a and 1044b are expressed as in Equations 49 and 50 where $r_s$, $r_p$, $t_p$ and $t_s$ are complex amplitude reflectance and complex amplitude transmittance to p-polarized light and s-polarized light of the parallel plate in the beam splitter means 1130, which have been calculated or measured in advance for corrective operation by the controller 1150, and a suffix * means a complex conjugate relationship:

$$I_1 = r_p^2 r_s^2 t_p^2 t_s^2 (E_1^* \cdot E_1) \tag{49}$$

$$I_2 = t_p^2 t_s^2 r_p^2 r_s^2 (E_2^* \cdot E_2) \tag{50}$$

Figure 13:
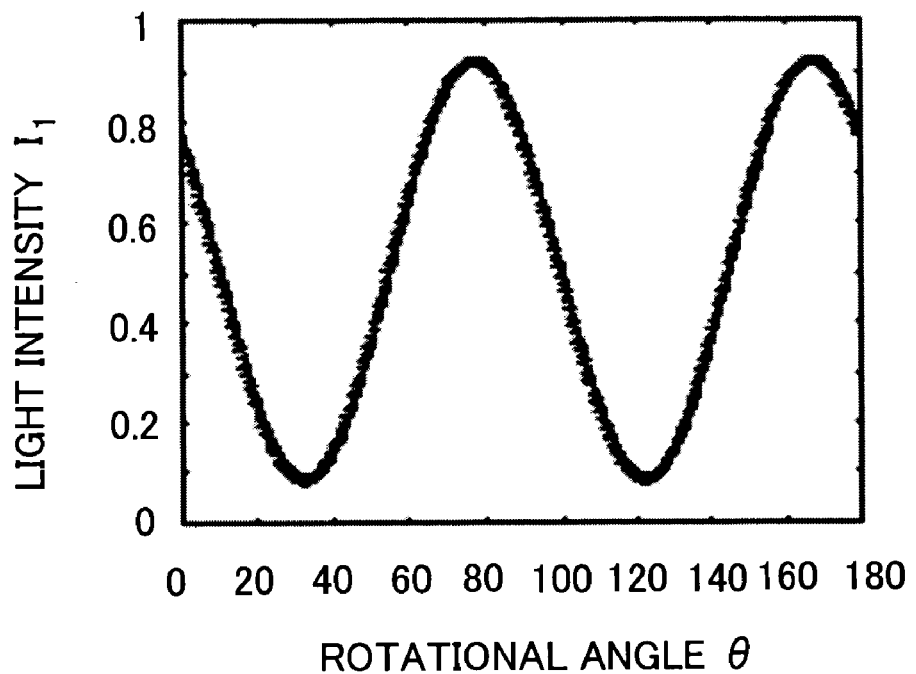
FIG. 13 is an exemplary graph a curve that changes like a sine curve of a light intensity $I_1$ to a rotational angle of a half-wave plate.
Figure 14:
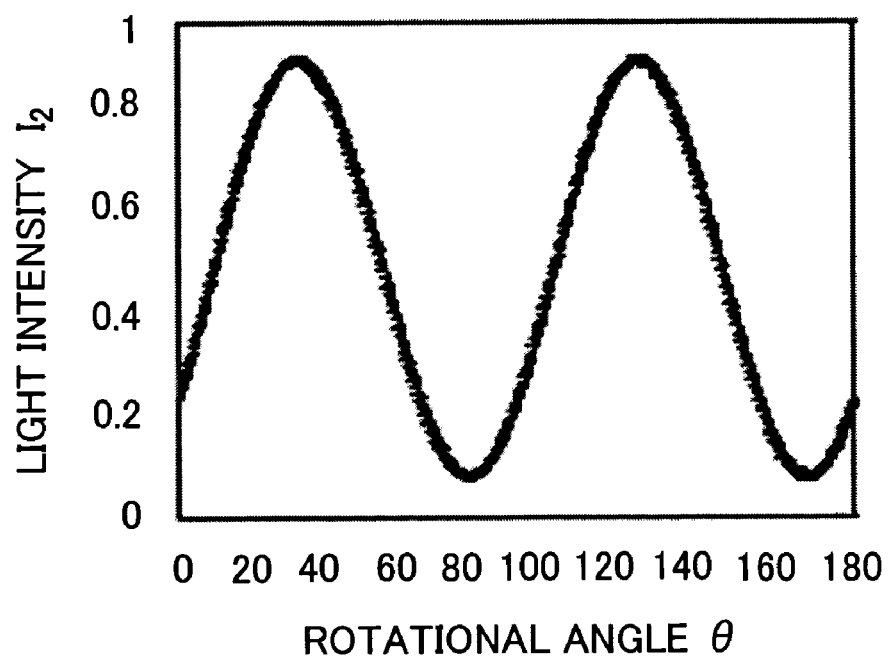
FIG. 14 is an exemplary graph a curve that changes like a sine curve of a light intensity $I_2$ to a rotational angle of a half-wave plate.

FIGS. 13 and 14 show graphs of exemplary sine variance curves of the light intensities $I_1$ and $I_2$ relative to the rotational angle θ of the half-wave plate 1024. FIGS. 13 and 14 set the light intensities $I_1$ and $I_2$ along the ordinate axis, and the rotational angle θ of the half-wave plate 1024 along the abscissa axis. Referring to FIGS. 13 and 14, the phase difference Δ of the object ST is calculated by Equation 45 using a ratio between the maximum and minimum values $I_{max}$ or $I_{min}$ of the light intensity $I_1$ or $I_2$:

$$\Delta = 90 - 2 \tan^{-1}(\sqrt{I_{min}/I_{max}}) \tag{45}$$

Figure 15:
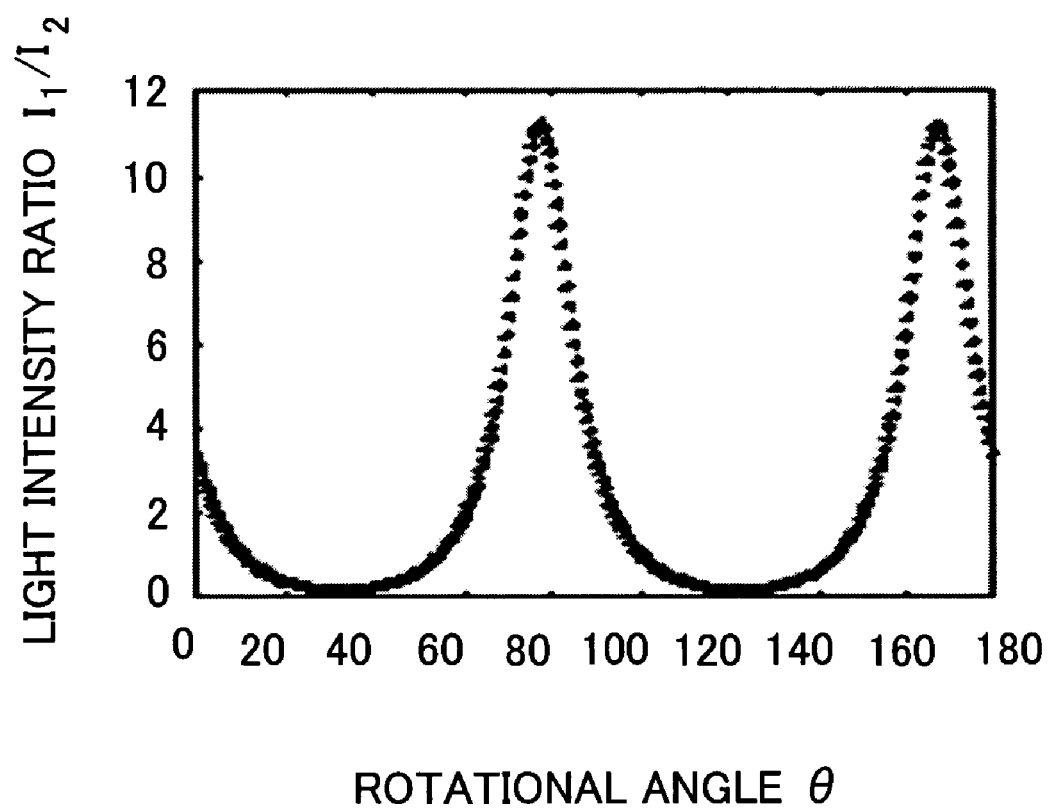
FIG. 15 is an exemplary graph of a variance curve of the light intensity ratio $I_1/I_2$ to a rotational angle of a half-wave plate.

The birefringence measurement apparatus 1100 equalizes light quantities between the first beam $L_1$ and the second beam $L_2$, and may output a ratio between the light intensities $I_1$ and $I_2$ received by the light-quantity detector means 1044a and 1044b. FIG. 15 is a graph of an exemplary variance curve of the ratio between the light intensities $I_1$ and $I_2$ relative to the rotational angle θ of the half-wave plate 1024. FIG. 15 sets a ratio between the light intensities $I_1$ and $I_2$ along the ordinate axis, and the rotational angle θ of the half-wave plate 1024 along the abscissa axis. Referring to FIG. 15, the phase difference Δ of the object ST is calculated by Equation 51 using the maximum and minimum values of the ratio between the light intensities $I_1$ and $I_2$, i.e., $(I_1/I_2)_{max}$ or $(I_1/I_2)_{min}$:

$$\Delta = 90 - 2 \tan^{-1}(\sqrt{(I_1/I_2)_{min}}) = 90 - 2 \tan^{-1}(\sqrt{1/(I_1/I_2)_{max}}) \tag{51}$$

The azimuth Φ of a fast axis of the object ST is calculated using Equation 46 where $\theta_1$ is a rotational angle of the half-wave plate 1024 when the ratio between the light intensities $(I_1/I_2)$ initially exhibits the minimum value $(I_1/I_2)_{min}$, and $\theta_2$ is a rotational angle of the half-wave plate 1024 when the ratio between the light intensities $(I_1/I_2)$ initially exhibits the maximum value $(I_1/I_2)_{max}$:

$$\Phi = 2\theta_1 - 45 = 2\theta_2 - 135 \tag{46}$$

The birefringence measurement apparatus 1100 uses the half-quarter plate 1024 as an optical element that is rotationally driven, and does not have to synchronize rotationally drive periods of two optical elements, for example, as in the conventional heterodyne method, thereby achieving precise birefringence measurement without influence of measurement errors, such as a synchronous offset. The equal light quantity of the first and second beams $L_1$ and $L_2$ split by the beam splitter means 1130 enables the two light-quantity detector means 1044a and 1044b to detect the light quantity in the same light-quantity range, thereby providing high S/N in detecting the light quantity and precise measurements. The measurement time may be shortened by simultaneously outputting the light-quantity ratio to the rotational angle θ of the half-wave plate 1024.

Ninth Embodiment

Figure 16:
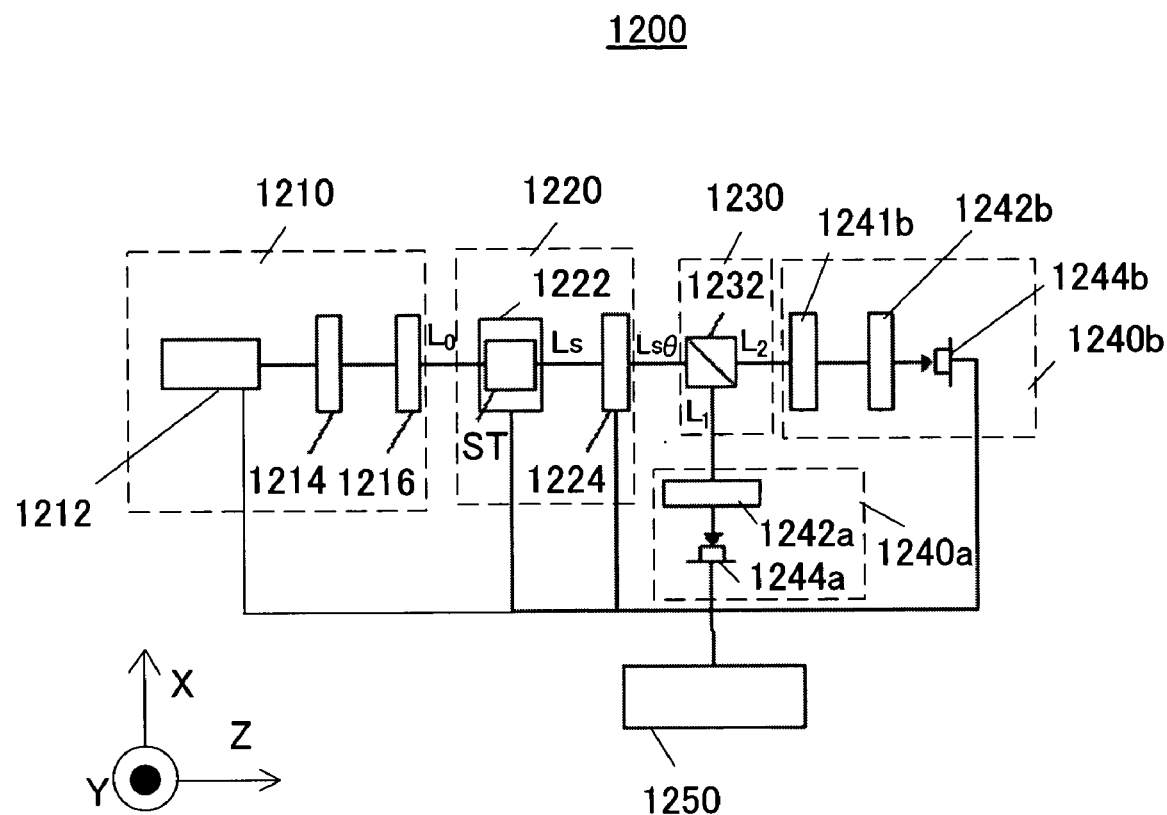
FIG. 16 is a schematic block diagram of a birefringence measurement apparatus of a ninth embodiment according to the present invention.

A description will be given of a birefringence measurement apparatus 1200 with reference to FIGS. 16 to 18. FIG. 16 is a schematic block diagram of the birefringence measurement apparatus 1200. FIG. 16 sets a Z-axis as a proceed direction of light emitted from a light source 1212, an X-axis as a direction perpendicular to the Z-axis on an installation surface of the light source 1212, and a Y-axis as a direction normal to the installation surface of the light source 1212.

The birefringence measurement apparatus 1200 serves to measure a retardation magnitude in an object to be measured ST, and includes, as shown in FIG. 16, a light source part 1210, a measurement part 1220, a beam splitter means 1230, detector parts 1240a and 1240b, and a controller 1250.

The light source part 1010 emits circularly polarized light to the object ST, and includes a light source 1212, a linear polarization element 1214, and a quarter-wave plate 1216.

The light source 1212 is a light source that emits a predetermined beam to the object ST, and includes, for example, a visible-range continuous laser, such as an output stabilized He-Ne laser, and an ultraviolet pulsed laser.

The linear polarization element 1214 is oriented with a polarization direction of 0° to a baseline axis preset around the optical axis and on an XY surface orthogonal to an optical-axis direction. The linear polarization element 1214 may use an optical element that separates orthogonal polarized light components and picks up one linearly polarized light component, such as a Glan-Thompson polarizing prism, a Rochon polarizing prism, a Senarmon polarizing prism, and a Wollaston polarizing prism or a polarization beam splitter made of dielectric multilayer, etc.

The quarter-wave plate 1216 is oriented with an azimuth of a fast axis of 45° to the baseline axis, and converts the polarization the light emitted from the light source 1212 to the circular polarized light $L_O$ and introduces the same to the object ST in cooperation with the linear polarization element 1214.

The measurement part 1220 has a stage 1222 that holds the object ST, and a half-wave plate 1224.

The stage 1222 has, for example, an XY stage, which may variably control a measurement position of the object ST manually or automatically on a surface orthogonal to the optical-axis direction. The stage 1222 controls positions of the object ST, and achieves the two-dimensional birefringence distribution on the measurement surface. The circularly polarized light $L_O$ that has transmitted through the object ST is converted into the elliptically polarized light $L_S$ having the birefringence information of the object ST.

The half-wave plate 1224 has a rotary mechanism, a rotation around the optical axis of which is controlled by a stepping motor (not shown), etc. The stepping motor is controlled based on a command of the controller 1250, which will be described later, and one cycle of birefringence measurement is a rotation from 0° to 180° in the azimuth of a fast axis relative to the baseline axis.

The half-wave plate 1224 serves to covert the rotation around the optical axis while maintaining the polarization of the incident light. Control over rotations of the half-wave plate 1224 converts the elliptically polarized light $L_S$ that has birefringence information of the object ST into a beam $L_{S\theta}$ that maintains the polarization of the beam $L_S$.

The beam splitter means 1230 is the same as the above beam splitter means 1030, and a detailed description will be omitted.

The detector 1240a includes a linear polarization element 1242a, and a light-quantity detector means 1244a, which the first beam $L_1$ enters. The linear polarization element 1242a is oriented so that its polarization direction is 0° to the baseline axis. The first beam $L_1$ is emitted as a light signal including the birefringence information representative of the retardation magnitude and azimuth of a principal axis of the object ST to the light-quantity detector means 1244a via the linear polarization element 1242a. The light-quantity detector means 1244a detects this light signal, and outputs a detection signal corresponding to the light intensity of the light signal to the controller 1250.

The detector 1240b includes a quarter-wave plate 1241b, a linear polarization element 1242b, and a light-quantity detector means 1244b, which the second beam $L_2$ enters. The quarter-wave plate 1241b and linear polarization elements 1242b are oriented so that their polarization directions are 45° to the baseline axis. The second beam $L_2$ is emitted as a light signal including the birefringence information representative of the retardation magnitude and azimuth of a principal axis of the object ST to the light-quantity detector means 1244b via the quarter-wave plate 1241b and linear polarization elements 1242b. The light-quantity detector means 1244b detects this light signal, and outputs a detection signal corresponding to the light intensity of the light signal to the controller 1250.

The controller 1250 stores a CPU and memory (not shown), and controls actions of each component in the birefringence measurement apparatus 1200, such as the light source 1212, stage 1222, and half-wave plate 1224. By executing a preset operational algorithm based on the detection signals detected by the light-quantity detector means 1244a and 1244b, the controller 1250 calculates a phase difference and an azimuth of a fast axis of the object ST. The controller 1250 may output the calculation result of the birefringence measurement to an output unit (not shown).

A description will be given of a birefringence measuring method using the birefringence measurement apparatus 1200. The light source part 1210 converts the linearly or elliptically polarized light emitted from the light source 1212 into horizontally linearly polarized light $E_O$ via the linear polarization element 1214 that is oriented with a polarization direction of 0° to a baseline axis. The polarization of the horizontally linearly polarized light $E_O$ is expressed using the Jones matrix as in Equation 25, and the polarization of the circularly polarized light $L_O$ emitted from the quarter-wave plate 1216 is expressed using the Jones matrix as in Equation 25:

$$E_0 = \begin{pmatrix} 1 \\ e^{-i\varphi} \end{pmatrix} \quad (25)$$

$$L_0 = R_{\pi/4} \times Q \times R_{-\pi/4} \times A_H \times E_0 \quad (52)$$

The circularly polarized light $L_O$ transmits through the object ST, and is converted into elliptically polarized light $L_s$ due to phase offset resulting from a difference of refractive index of two principal axes of the object ST, i.e., a fast axis and a slow axis. The phase difference Δ and the azimuth of a principal axis Φ of the object ST and the Jones matrix S of the object ST are expressed as in Equation 10:

$$S = \begin{pmatrix} \cos(\phi) & -\sin(\phi) \\ \sin(\phi) & \cos(\phi) \end{pmatrix} \begin{pmatrix} \exp(i*\Delta/2) & 0 \\ 0 & \exp(-i*\Delta/2) \end{pmatrix} \begin{pmatrix} \cos(\phi) & \sin(\phi) \\ -\sin(\phi) & \cos(\phi) \end{pmatrix} \quad (10)$$

The polarization of the elliptically polarized light $L_S$ is expressed as in Equation 38 using the Jones vector S:

$$Ls = S \times L_0 \quad (38)$$

The Jones matrix H of the half-wave plate 1224 is expressed as in Equation 39:

$$H = \begin{pmatrix} \exp(i*\pi/2) & 0 \\ 0 & \exp(-i*\pi/2) \end{pmatrix} \quad (39)$$

As the half-wave plate 1224 is rotationally driven around the optical axis by the controller 1250, the Jones matrix $R_\theta$ of the rotational conversion is expressed as in Equation 11 where θ is a rotational angle from an origin that is a position where the azimuth of a fast axis is 0° relative to the baseline axis:

$$R_\theta = \begin{pmatrix} \cos(\theta) & -\sin(\theta) \\ \sin(\theta) & \cos(\theta) \end{pmatrix} \quad (11)$$

The half-wave plate 1224 rotationally converts the elliptically polarized light $L_S$ having the birefringence information into the beam $L_{S\theta}$ while maintaining the polarization, and the polarization of the beam $L_{S\theta}$ is expressed as in Equation 40 using the Jones vector:

$$L_{S\theta} = R_\theta \times H \times R_{-\theta} \times L_S \quad (40)$$

The beam splitter means 1230 splits the light $L_{S\theta}$ having the birefringence information of the object ST into the first and second beams $L_1$ and $L_2$ while maintaining the polarization of the light $L_{S\theta}$. The polarization of the first and second beams $L_1$ and $L_2$ are expressed as in Equations 53 and 54 using the Jones vector where $r_s$, $r_p$, $t_p$ and $t_s$ are complex amplitude reflectance and complex amplitude transmittance to p-polarized light and s-polarized light of the parallel plate in the beam splitter means 1030, which have been calculated or measured in advance for corrective operations by the controller 1250:

$$L_1 = r_s r_p L_{S\theta} \quad (53)$$

$$L_2 = t_s t_p L_{S\theta} \quad (54)$$

The first beam $L_1$ enters the light-quantity detector means 1244a via the linear polarization element 1242a that is oriented with its polarization direction at 0° relative to the baseline axis. The second beam $L_2$ enters the light-quantity detector means 1244b via the quarter-wave plate 1241b and linear polarization element 1242b that are oriented with its polarization direction at 45° relative to the baseline axis.

The polarizations of the first and second beams $L_1$ and $L_2$ received by the light-quantity detector means 1244a and 1244b are expressed as in Equations 41 and 55 using the Jones vectors:

$$E_1 = A_H Ls \quad (41)$$

$$E_2 = R_{\pi/4} \times A_H \times R_{-\pi/4} \times R_{\pi/4} Q \times R_{-\pi/4} \times L_2 \quad (55)$$

The light-quantity detector means 1244a and 1244b detect light signals of the beams $L_1$ and $L_2$, and output detection signals corresponding to their light intensities to the operation part 1250. The corrected light intensities $I_1$ and $I_2$ detected by the light-quantity detector means 1244a and 1244b are expressed as in Equations 20 and 21 where a suffix * means a complex conjugate relationship:

$$I_1 = (E_1^* \cdot E_1)/|r_s r_p|^2 \quad (20)$$

$$I_2 = (E_2^* \cdot E_2)/|t_s t_p|^2 \quad (21)$$

The light intensities $I_1$ and $I_2$ received by the light-quantity detector means 1244a and 1244b vary like a sine curve with rotational angle θ of the half-wave plate 1224. The controller 1250 monitors the light intensity $I_1$ to rotational angle θ of the half-wave plate 1224, and may calculate ellipticity of birefringence ellipsoid representative of the birefringence information of the object ST. The controller 1250 monitors the light intensity $I_2$ to the rotational angle θ of the half-wave plate 1224, and distinguishes the fast axis from the slow axis representative of the birefringence information of the object ST.

Figure 17:
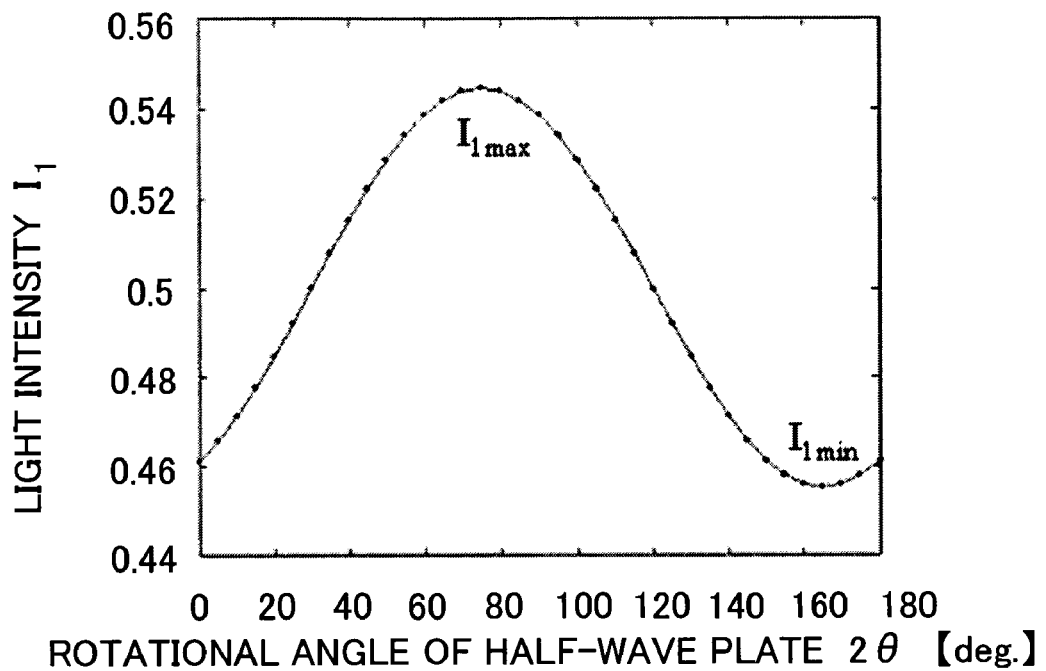
FIG. 17 is an exemplary graph a curve of a light intensity $I_1$ to a rotational angle of a half-wave plate.
Figure 18:
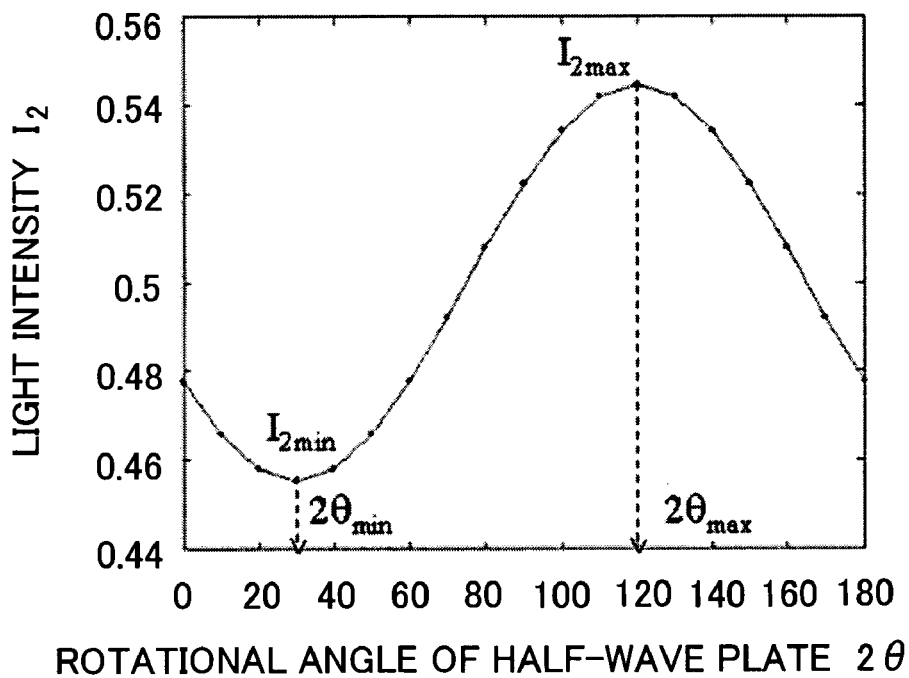
FIG. 18 is an exemplary graph a curve of a light intensity $I_2$ to a rotational angle of a half-wave plate.

FIGS. 17 and 18 show exemplary graphs of the light intensities $I_1$ and $I_2$ relative to the rotational angle θ of the half-wave plate 1224. The calculation condition sets the retardation magnitude Re=3 nm/cm and fast axis angle Az=30° of the object ST having a thickness d of 3 cm for a wavelength of 633 nm.

In FIG. 17, the phase difference Δ [deg.] of the object ST is calculated by Equation 56 using maximum and minimum values $I_{1max}$ and $I_{1min}$ of the light intensity $I_1$ to the rotational angle θ (0<2θ<180) [deg.] of the half-wave plate 1224:

$$\Delta = |90 - 2\tan^{-1}(\sqrt{I_{1min}/I_{1max}})| \quad (56)$$

The retardation magnitude Re [nm/cm] of the object ST is expressed as in Equation 24 where λ [nm] is a wavelength of the light source 1212 and d [cm] is a thickness of the object ST:

$$Re = \Delta \lambda / 360 d \quad (24)$$

In FIG. 18, the azimuth of a fast axis Φf [deg.] and azimuth of a slow axis Φs [deg.] of the object ST are calculated by Equations 57 and 58 where $2\theta_{max}$ and $2\theta_{min}$ are maximum and minimum angles of the light intensity $I_2$ to the rotational angle θ (0<2θ<180) [deg.] of the half-wave plate 1224:

$$\phi_f = 2\theta_{min} \quad (57)$$

$$\phi_s = 2\theta_{max} \quad (58)$$

The birefringence measurement apparatus 1200 uses the beam splitter means 1230 that splits light while maintaining its polarization, and detects birefringence information of the object ST with two or more detectors, thereby simultaneously measuring the retardation magnitude and the azimuth of a principal axis of the object ST with a simple apparatus configuration.

The birefringence measurement apparatus 1200 may not only measure the retardation magnitude and azimuth of a principal axis of the object ST, but also distinguish the fast axis and slow axis of the azimuth of a principal axis.

The birefringence measurement apparatus 1200 uses the half-quarter plate 1224 as an optical element that is rotationally driven, and does not have to synchronize rotationally drive periods of two optical elements, for example, as in the conventional heterodyne method, thereby achieving precise birefringence measurement without influence of measurement errors, such as a synchronous offset.

Tenth Embodiment

Figure 19:
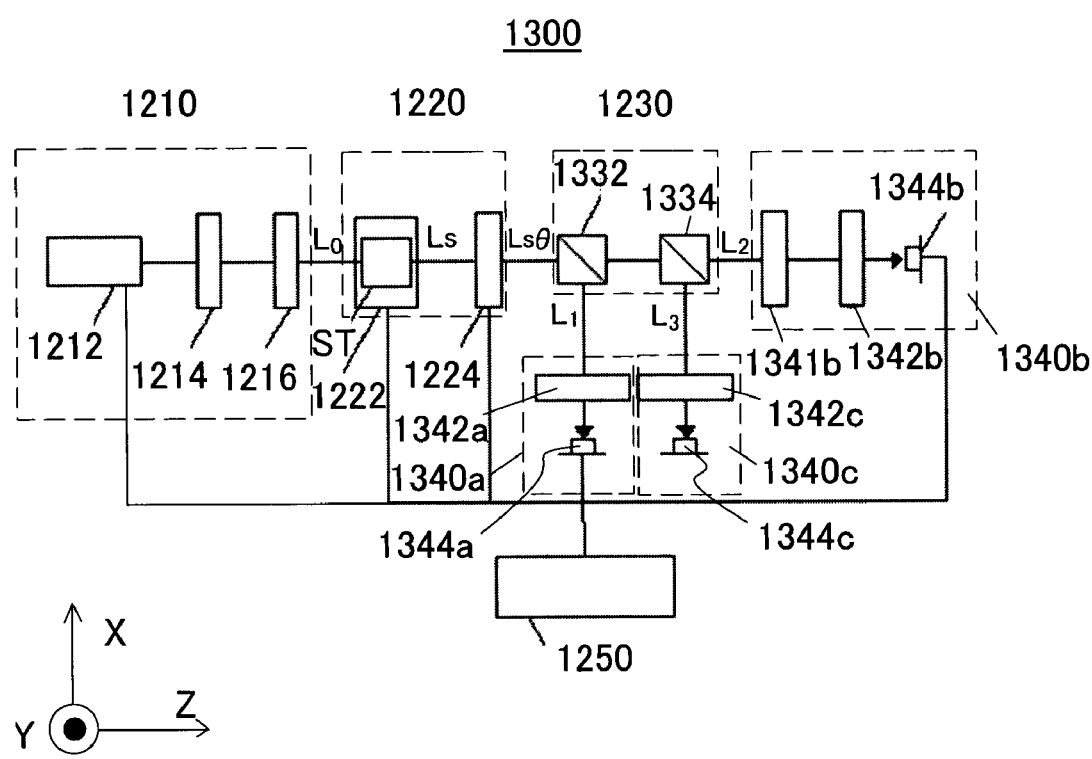
FIG. 19 is a schematic block diagram of a birefringence measurement apparatus of a tenth embodiment according to the present invention.

A description will be given of a birefringence measurement apparatus 1300 of a tenth embodiment according to the present invention with reference to FIGS. 19 to 22. FIG. 19 is a schematic block diagram of the birefringence apparatus 1300. The birefringence apparatus 1300 has the same structure as that of the birefringence apparatus 1200 except that the birefringence apparatus 1300 includes the beam splitter means 1330 structurally different from the beam splitter means 1230, and a detector part 1340c.

The birefringence measurement apparatus 1300 includes, as shown in FIG. 19, the light source part 1210, the measurement part 1220, the beam splitter means 1330, detector parts 1340a, 1340b and 1340c, and the controller 1250.

The beam splitter means 1330 includes beam splitter parts 1332 and 1334, each including three parallel plates arranged so that beams may enter at incident angle of 45°, serves to split the incident light into two beams while maintaining the polarization of the incident light. The beam splitter parts 1332 and 1334 splits light $L_{S\theta}$ having the birefringence information of the object ST into the first, second and third beams $L_1$, $L_2$ and $L_3$ while maintaining the polarization of the light $L_{S\theta}$. The first beam $L_1$ is incident upon the detector part 1340a, the second beam $L_2$ is incident upon the detector part 1340b, and the third beam $L_3$ is incident upon the detector part 1340c.

The detector part 1340c includes a linear polarization element 1342c and light-quantity detector means 1344c. The linear polarization element 1342c is oriented with a polarization direction of 90° relative to the baseline axis. The third beam $L_3$ is emitted as a light signal including the birefringence information representative of the retardation magnitude and azimuth of a principal axis of the object ST to the light-quantity detector means 1344c via the linear polarization element 1342c.

By executing a preset operational algorithm based on the detection signals detected by the light-quantity detector means 1344a, 1344b and 1344c, the controller 1250 calculates a phase difference and an azimuth of a fast axis.

A description will be given of a birefringence measurement method using the birefringence measurement apparatus 1300 as to differences from the birefringence measurement method using the birefringence measurement apparatus 1200.

The beam splitter parts 1332 and 1334 in the beam splitter means 1300A split the light $L_{S\theta}$ having the birefringence information of the object ST into the first, second and third beams $L_1$, $L_2$ and $L_3$. A description of the first and second beams $L_1$ and $L_2$ is omitted since it is similar to the description for the birefringence measurement apparatus 1200.

The polarizations of the first, second and third beams $L_1$, $L_2$ and $L_3$ are expressed as in Equations 53, 59 and 60 where $r_s$, $r_p$, $t_p$ and $t_s$ are complex amplitude reflectance and complex amplitude transmittance to p-polarized light and s-polarized light of the parallel plate in the beam splitter means 1330, which have been calculated or measured in advance for corrective operation in the operation part 1250:

$$L_1 = r_s r_p L_{S\theta} \tag{53}$$

$$L_2 = t_s t_p t_s t_p L_{S\theta} \tag{59}$$

$$L_3 = r_s r_p t_s t_p L_{S\theta} \tag{60}$$

The first beam $L_1$ enters the light-quantity detector means 1344a via the linear polarization element 1342a that is oriented with the polarization direction of 0° relative to the baseline axis. The third beam $L_3$ enters the light-quantity detector means 1344c via the linear polarization element 1342c that is oriented with its polarization direction at 90° relative to the baseline axis. The second beam $L_2$ enters the light-quantity detector means 1344b via the quarter-wave plate 1341b and linear polarization element 1342b that are oriented with their polarization directions at 45° relative to the baseline axis.

The polarizations of the first and second beams $L_1$, $L_2$ and $L_3$ received by the light-quantity detector means 1344a, 1344b and 1344c are expressed as in Equations 61, 55 and 62 using the Jones vectors:

$$E_1 = A_H \times L_1 \tag{61}$$

$$E_2 = R_{\pi/4} \times A_H \times R_{-\pi/4} \times R_{\pi/4} \times Q \times R_{-\pi/4} \times L_2 \tag{55}$$

$$E_3 = R_{\pi/2} \times A_H \times R_{-\pi/2} \times L_3 \tag{62}$$

The light-quantity detector means 1344a, 1344b and 1344c detect light signals of the beams $L_1$, $L_2$ and $L_3$, and output detection signals corresponding to their light intensities to the operation part 1250. The corrected light intensities $I_1$, $I_3$ and $I_2$ detected by the light-quantity detector means 1344a, 1344c and 1344b are expressed as in Equations 20, 63 and 64 where a suffix * means a complex conjugate relationship:

$$I_1 = (E_1^* \cdot E_1)/|r_s r_p|^2 \tag{20}$$

$$I_3 = (E_3^* \cdot E_3)/|r_s r_p t_s t_p|^2 \tag{63}$$

$$I_2 = (E_2^* \cdot E_2)/|t_s t_p t_s t_p|^2 \tag{64}$$

The light intensities $I_1$, $I_2$ and $I_3$ received by the light-quantity detector means 1344a, 1344b and 1344c vary like a sine curve with rotational angle θ of the half-wave plate 1224. The controller 1250 monitors a ratio between the light intensities $I_1$ and $I_3$ to rotational angle θ of the half-wave plate 1224, and may calculate ellipticity of birefringence ellipsoid representative of the birefringence information of the object ST. The controller 1250 monitors the light intensity $I_2$ to the rotational angle θ of the half-wave plate 1224, and distinguishes the fast axis from the slow axis representative of the birefringence information of the object ST.

Figure 20:
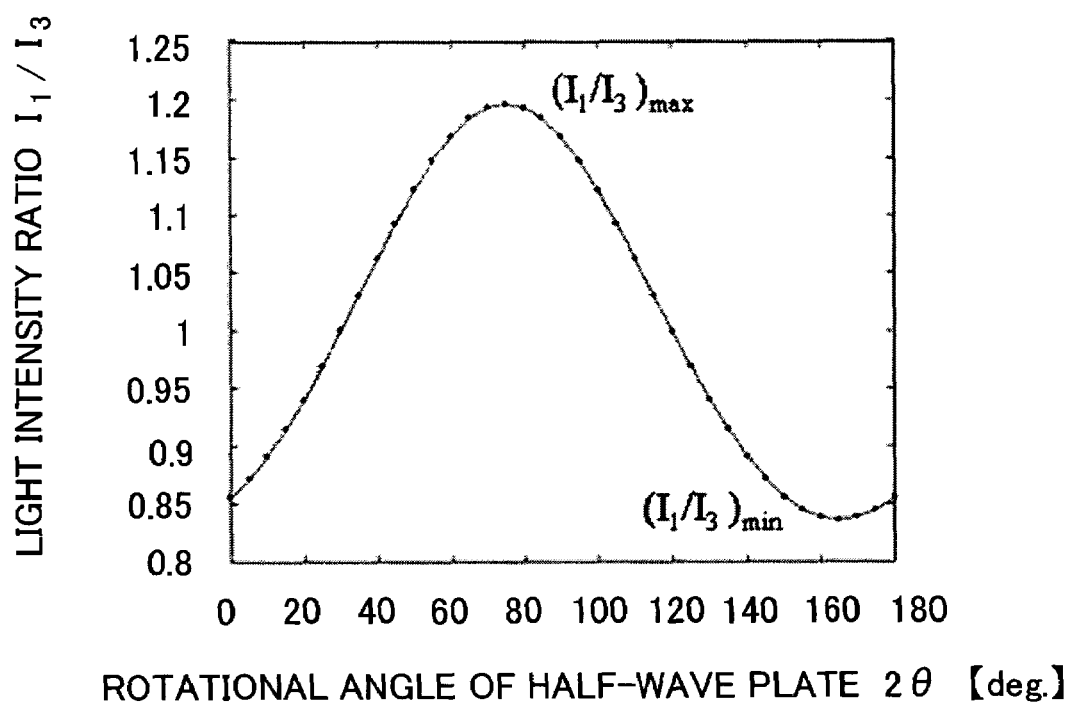
FIG. 20 is an exemplary graph of a variance curve of the light intensity ratio $I_1/I_3$ to a rotational angle of a half-wave plate.
Figure 22:
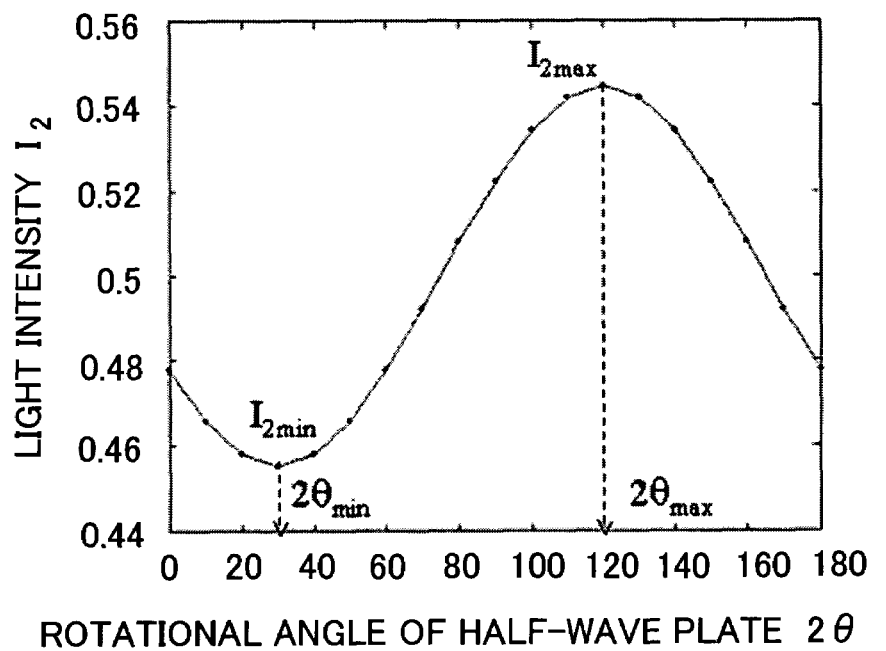
FIG. 22 is an exemplary graph a curve of a light intensity $I_2$ to a rotational angle of a half-wave plate.

FIGS. 20 and 22 show exemplary graphs of a ratio between the light intensities $I_1$ and $I_3$ and the light intensity $I_2$ relative to the rotational angle θ of the half-wave plate 1224. The calculation condition sets the retardation magnitude Re=3 nm/cm and fast axis angle Az=30° of the object ST having a thickness d of 3 cm for a wavelength of 633 nm.

In FIG. 20, the phase difference Δ [deg.] of the object ST is calculated by Equations 65 and 66 using maximum and minimum values $(I_1/I_3)_{max}$ and $(I_1/I_3)_{min}$ of the ratio $(I_1/I_3)$ between the light intensities $I_1$ and $I_3$:

$$\Delta = |90 - 2\tan^{-1}(\sqrt{(I_1/I_3)_{max}})| \tag{65}$$

$$\Delta = |90 - 2\tan^{-1}(\sqrt{1/(I_1/I_3)_{min}})| \tag{66}$$

The retardation magnitude Re [nm/cm] of the object ST is expressed as in Equation 24 where λ [nm] is a wavelength of the light source 1212 and d [cm] is a thickness of the object ST:

$$Re = \Delta\lambda/360d \tag{24}$$

Figure 21:
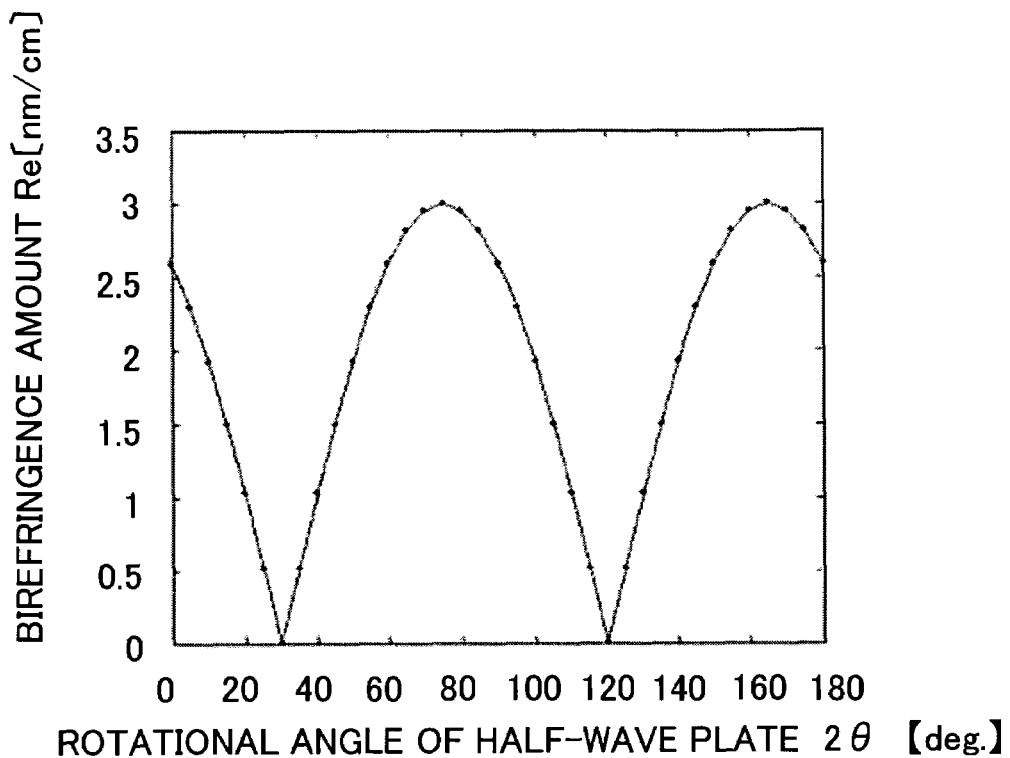
FIG. 21 is an exemplary graph of a variance curve of the light intensity ratio $I_1/I_3$ to a rotational angle of a half-wave plate.

FIG. 21 is a graph of the ratio between light intensities $I_1/I_3$ relative to the rotational angle θ of the half-wave plate 1224 (0<2θ<180) [deg.], which has been converted into the retardation magnitude Re [nm/cm] using the Equation 38.

In FIG. 22, the azimuth of a fast axis Φf [deg.] and azimuth of a slow axis Φs [deg.] of the object ST are calculated by Equations 57 and 58 where $2\theta_{max}$ and $2\theta_{min}$ are maximum and minimum angles of the light intensity $I_2$ to the rotational angle θ (0<2θ<180) [deg.] of the half-wave plate 1224:

$$\Phi_f = 2\theta_{min} \tag{57}$$

$$\Phi_s = 2\theta_{max} \tag{58}$$

The birefringence measurement apparatus 1300 uses the beam splitter means 1330 that splits light while maintaining its polarization, and detects birefringence information of the object ST with two or more detectors, thereby simultaneously measuring the retardation magnitude and the azimuth of a principal axis of the object ST with a simple apparatus configuration. The birefringence measurement apparatus 1300 may not only measure the retardation magnitude and azimuth of a principal axis of the object ST, but also distinguish the fast axis and slow axis of the azimuth of a principal axis. The birefringence measurement apparatus 1300 may simultaneously measure the maximum and minimum amounts of the light $L_{Sθ}$ having the birefringence information of the object ST as the ratio between the light intensities $I_1$ and $I_3$, thereby providing precise measurements without influence of light-quantity fluctuation of the light source 1212, etc.

The birefringence measurement apparatus 1300 uses the half-quarter plate 1224 as an optical element that is rotationally driven, and does not have to synchronize rotationally drive periods of two optical elements, for example, as in the conventional heterodyne method, thereby achieving precise birefringence measurement without influence of measurement errors, such as a synchronous offset. The birefringence measurement apparatus 1300 may cancel out the influence of manufacture errors, etc. of the optical elements by averaging plural retardation magnitudes operated at an interval of 90° as the half-wave plate 1224 rotates. The retardation magnitude is fed back to the controller 1250 and the sampling number of a rotational angle range and measurement data is controlled for locally precise measurements according to the retardation magnitude of the object ST.

Eleventh Embodiment

Figure 23:
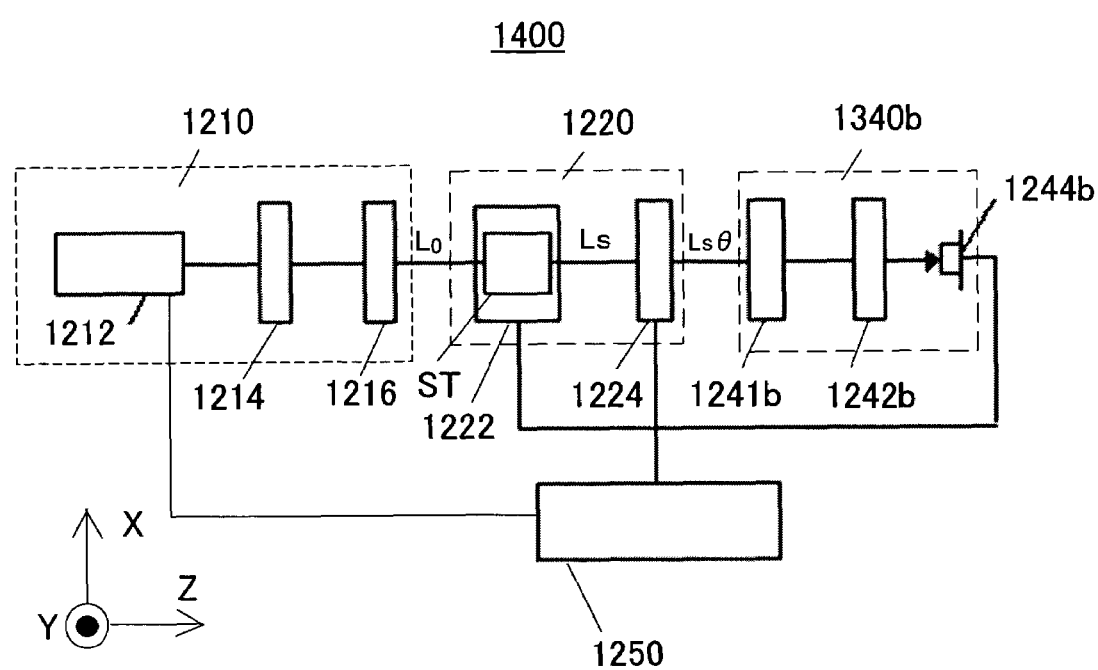
FIG. 23 is a schematic block diagram of a birefringence measurement apparatus of an eleventh embodiment according to the present invention.

A description will be given of a birefringence measurement apparatus 1400 of an eleventh embodiment according to the present invention with reference to FIGS. 23 and 24. FIG. 23 is a schematic block diagram of the birefringence apparatus 1400. The birefringence apparatus 1400 has the same structure as that of the birefringence apparatus 1200 except that the birefringence apparatus 1400 does not include the beam splitter means 1230 or the detector part 1340a.

The birefringence measurement apparatus 1400 includes, as shown in FIG. 23, the light source part 1210, the measurement part 1220, detector parts 1340b, and the controller 1250.

The light emitted from the light source 1212 is converted into circularly polarized light $L_O$ by the linear polarization element 1214 and quarter-wave plate 1216. The circularly polarized light $L_O$ turns to elliptically polarized light $L_S$ including birefringence information after entering the object ST, and then is rotationally converted into the light $L_{Sθ}$ that maintains the polarization of the elliptically polarized light $L_S$ by the half-wave plate 1224 that is rotationally driven. The light $L_{Sθ}$ enters the light-quantity detector means 1244b via the quarter-wave plate 1241b and linear polarization element 1242b that are oriented with polarization directions at 45° relative to the baseline axis.

A description will be given of a birefringence measurement method using the birefringence measurement apparatus 1400 as to differences from the birefringence measurement method using the birefringence measurement apparatus 1200. The polarization of the light $L_{Sθ}$ received by the light-quantity detector means 1244b is expressed as in Equation 67:

$$E = R_{\pi/4} \times A_H \times R_{-\pi/4} \times R \times R_{\pi/4} \times Q \times R_{-\pi/4} 33 \, L_{Sθ} \tag{67}$$

The light-quantity detector means 1244b detects a light signal of the light $L_{Sθ}$, and outputs a detection signal corresponding to its light intensity to the operation part 1250. The light intensity I detected by the light-quantity detector means 1244b is expressed as in Equation 68 where a suffix * means a complex conjugate relationship:

$$I = E^* \cdot E \tag{68}$$

The light intensity I received by the light-quantity detector means 1244b varies like a sine curve with rotational angle θ of the half-wave plate 1224. The controller 1250 monitors the light intensity I to the rotational angle θ of the half-wave plate 1224, and may calculate ellipticity of birefringence ellipsoid representative of the birefringence information of the object ST, as well as distinguishing the fast axis from the slow axis in the principal axes.

Figure 24:
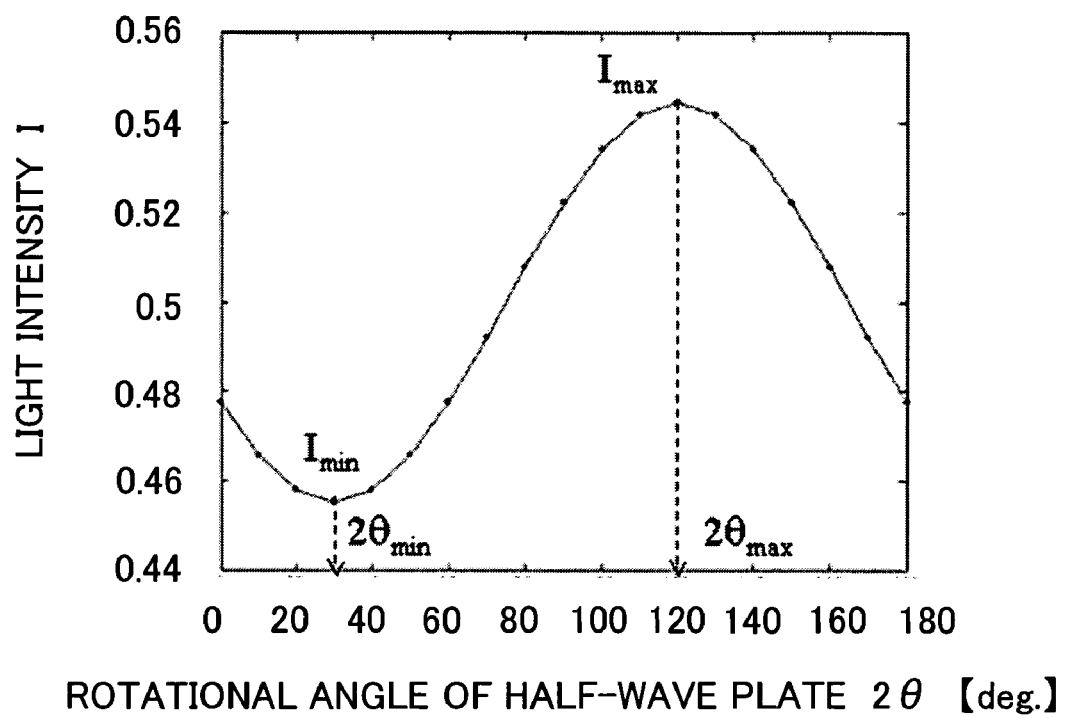
FIG. 24 is an exemplary graph a curve of a light intensity I to a rotational angle of a half-wave plate.

FIG. 24 shows an exemplary graph of the light intensity I to the rotational angle θ of the half-wave plate 1224. The calculation condition sets the retardation magnitude Re=3 nm/cm and fast axis angle Az=30° of the object ST having a thickness d of 3 cm for a wavelength of 633 nm.

In FIG. 24, the phase difference Δ [deg.], an azimuth of a fast axis Φf [deg.], and an azimuth of a slow axis Φs [deg.] of the object ST are calculated by Equations 69, 57 and 58, respectively, where $I_{max}$ and $I_{min}$ are maximum and minimum values of the light intensity I to the rotational angle θ [deg.] (0<2θ<180) of the half-wave plate 1224, and $2\theta_{max}$ and $2\theta_{min}$ are rotational angles of the half-wave plate 1224:

$$\Delta = |90 - 2\tan^{-1}(\sqrt{I_{min}/I_{max}})| \tag{69}$$

$$\Phi_f = 2\theta_{min} \tag{57}$$

$$\Phi_s = 2\theta_{max} \tag{58}$$

The retardation magnitude Re [nm/cm] of the object ST is expressed as in Equation 24 where λ [nm] is a wavelength of the light source 1212 and d [cm] is a thickness of the object ST:

$$Re = \Delta\lambda/360d \tag{24}$$

The birefringence measurement apparatus 1400 may not only measure the retardation magnitude and azimuth of a principal axis of the object ST, but also distinguish the fast axis and slow axis of the azimuth of a principal axis. The birefringence measurement apparatus 1400 uses the half-quarter plate 1224 as an optical element that is rotationally driven, and does not have to synchronize rotationally drive periods of two optical elements, for example, as in the conventional heterodyne method, thereby achieving precise birefringence measurement without influence of measurement errors, such as a synchronous offset.

Twelfth Embodiment

Figure 25:
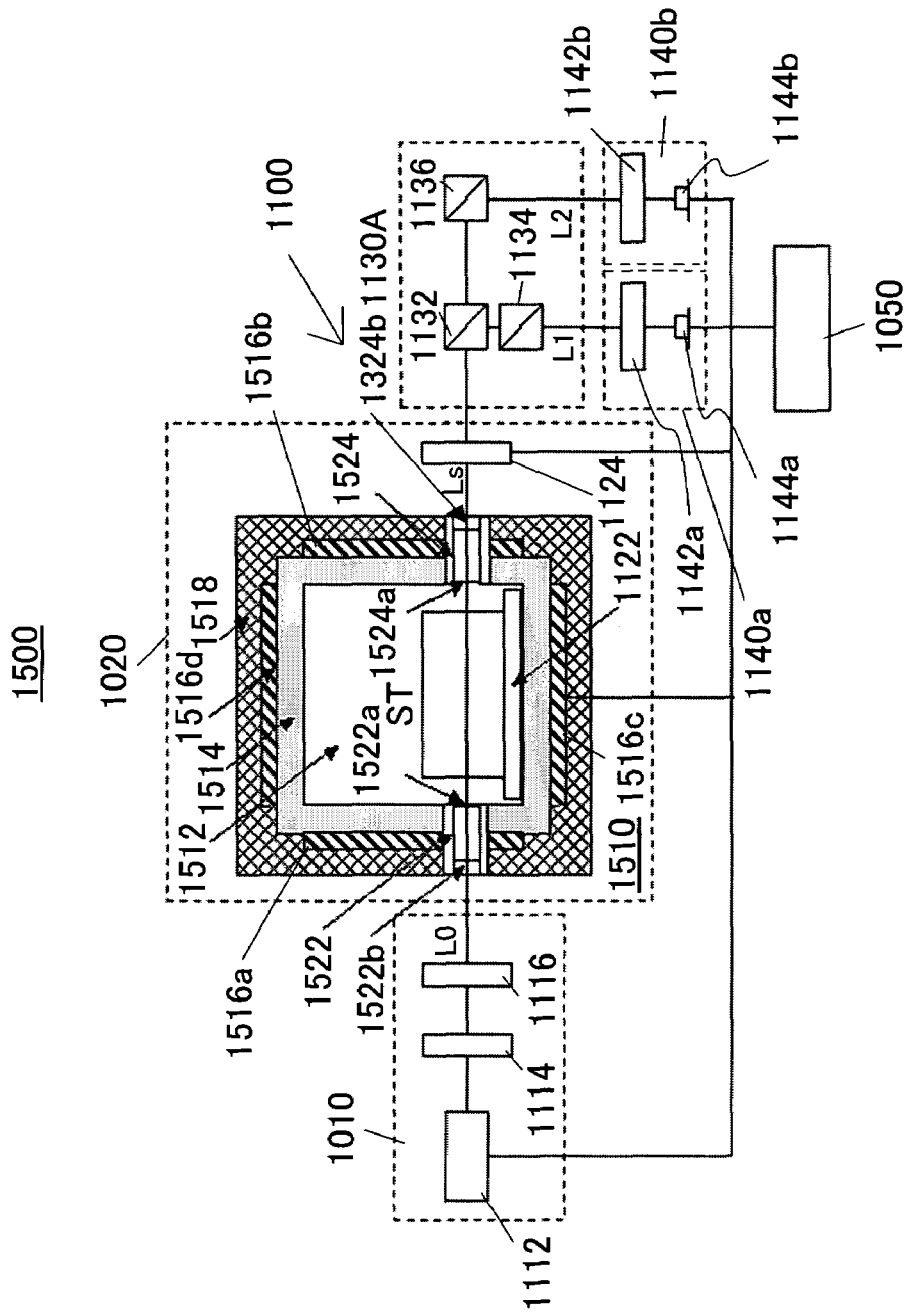
FIG. 25 is a schematic block diagram of a strain remover of another aspect of the present invention.

A description will be given of a strain remover 1500 of a twelfth embodiment according to the present invention with reference to FIG. 25. FIG. 25 is a schematic block diagram of the strain remover 1500.

The strain remover 1500 includes, as shown in FIG. 25, the birefringence measurement apparatus 1100, and a heat treatment part 1510, and removes the retardation magnitude in an optical element as the object ST. The strain remover 1500 exemplarily applies the birefringence measurement apparatus 1100, but may apply other types of birefringence measurement apparatuses.

The heat treatment part 1510 heat-treats the object ST to remove the retardation magnitude in the object ST. The heat treatment part 1510 is provided in the measurement part 1020 in the birefringence measurement apparatus 1100, and includes a stainless container 1514 having a storage chamber 1512 for storing the object ST, plural heating units 1516a to 1516d each of which has an independently temperature controllable heater on side, bottom, and upper parts of the stainless container 1514, and an adiabatic wall 1518 that encloses the heating units 1516a to 1516d.

The temperature in the storage chamber 1512 is controllable by the controller 1050. The object ST housed in the stainless container 1514 may be uniformly heat-treated by independently controlling the temperature of the heating units 1516a to 1516d installed around the stainless container 1514, and reducing temperature non-uniformity in the storage chamber 1512.

The controller 1050 monitors the birefringence changes of the optical element as the object ST in the heat treatment step, and controls the heat treatment conditions, such as temperature, holding time, temperature rise speed, and cooling speed, so that the retardation magnitude may be within the desired range. A separate temperature controller may be provided in addition to the controller 1050.

The heat treatment part 1510 is provided with a light guide tube 1522 for introducing circularly polarized light $L_o$ emitted from the light source 1010 into the storage chamber 1512, and a light guide tube 1524 for introducing transmitting light $L_s$ of the object ST to the outside the storage chamber 1512. The light guide tubes 1522 and 1524 are provided with transparent shutters 1522a and 1524a for shielding the atmosphere in the storage chamber 1512 from the outside, transparent quartz window or calcium-fluoride window 1522b, 1524b, etc.

The strain remover 1500 may measure changes in retardation magnitude in the heat treatment step of the optical element as the object ST, and remove the retardation magnitude of the object ST and shorten the heat treatment time by enabling the controller 1050 to feedback-control the heat treatment conditions based on the measurement result.

Thirteenth Embodiment

Figure 26:
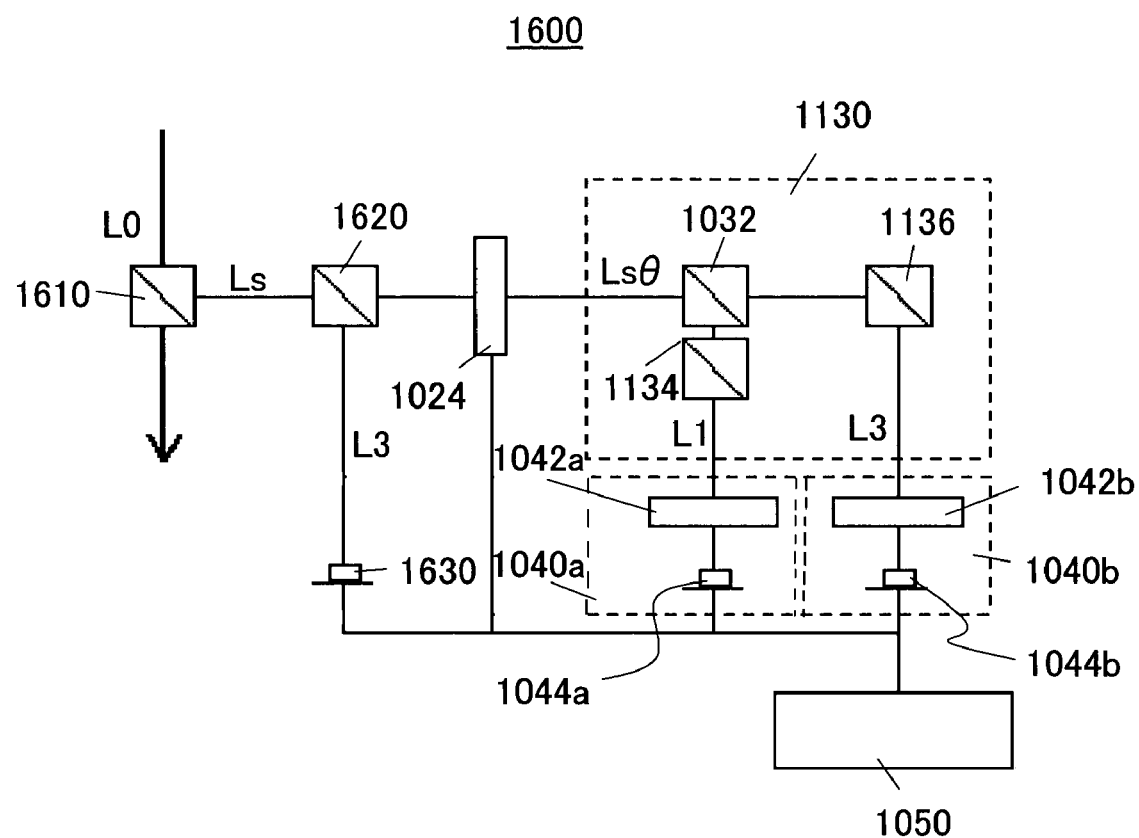
FIG. 26 is a polarization measurement apparatus of another aspect of the present invention.

A description will be given of a polarimeter 1600 of a thirteenth embodiment according to the present invention with reference to FIG. 26. FIG. 26 is a block diagram of the polarimeter 1600.

The polarimeter 1600 measures the light quantity and polarization of light to be measured, such as illumination light in an exposure apparatus. The polarimeter 1600 of the instant embodiment uses the birefringence measurement apparatus 1100 except for the light source part 1010 and the stage 1022 of the measurement part 1020, but the present invention does not restrict other birefringence measurement apparatuses to be applied.

The polarimeter 1600 includes, as shown in FIG. 26, beam splitter parts 1610 and 1620 structurally similar to the beam splitter part 1032 etc., beam splitter means 1130, detectors 1040a and 1040b, light quantity detector means 1630, and controller 1050.

The beam splitter part 1610 arranged in the optical path of the light $L_O$ in the polarimeter 1600 splits the light $L_O$ to be measured, into light $L_S$ that maintains the polarization of the light $L_O$. The beam splitter part 1620 then splits the light $L_s$ into a transmission beam and a reflection beam $L_3$. The transmission beam split by the beam splitter part 1620 is split into the beams $L_1$ and $L_2$ via the half-wave plate 1024 having a rotary mechanism, and the beam splitter part 1032.

The light $L_3$ is incident as a light signal including a light amount fluctuation of the light $L_O$ upon the light-quantity detector means 1630. The light-quantity detector means 1630 detects this light signal, and outputs a detection signal corresponding to the light intensity to the controller 1050.

The controller 1050 includes a CPU and memory (not shown), and controls actions of the half-wave plate 1024. The controller 1050 calculates the light quantity and polarization of the light $L_o$ based on the detection signal detected by the light-quantity detector means 1044a, 1044b and 1630. The controller 1050 may output a calculation result of the light quantity and polarization of the light $L_O$ to an output unit (not shown).

Therefore, the exposure apparatus having the polarimeter 400, for example, may detect the accurate exposure dose, always detect the polarization of the illumination optical system, and accurately feedback-control the exposure dose, irrespective of the varying polarization characteristic of the illumination optical system. Use of this exposure apparatus would improve the throughput and provide high-quality devices.

Figure 27:
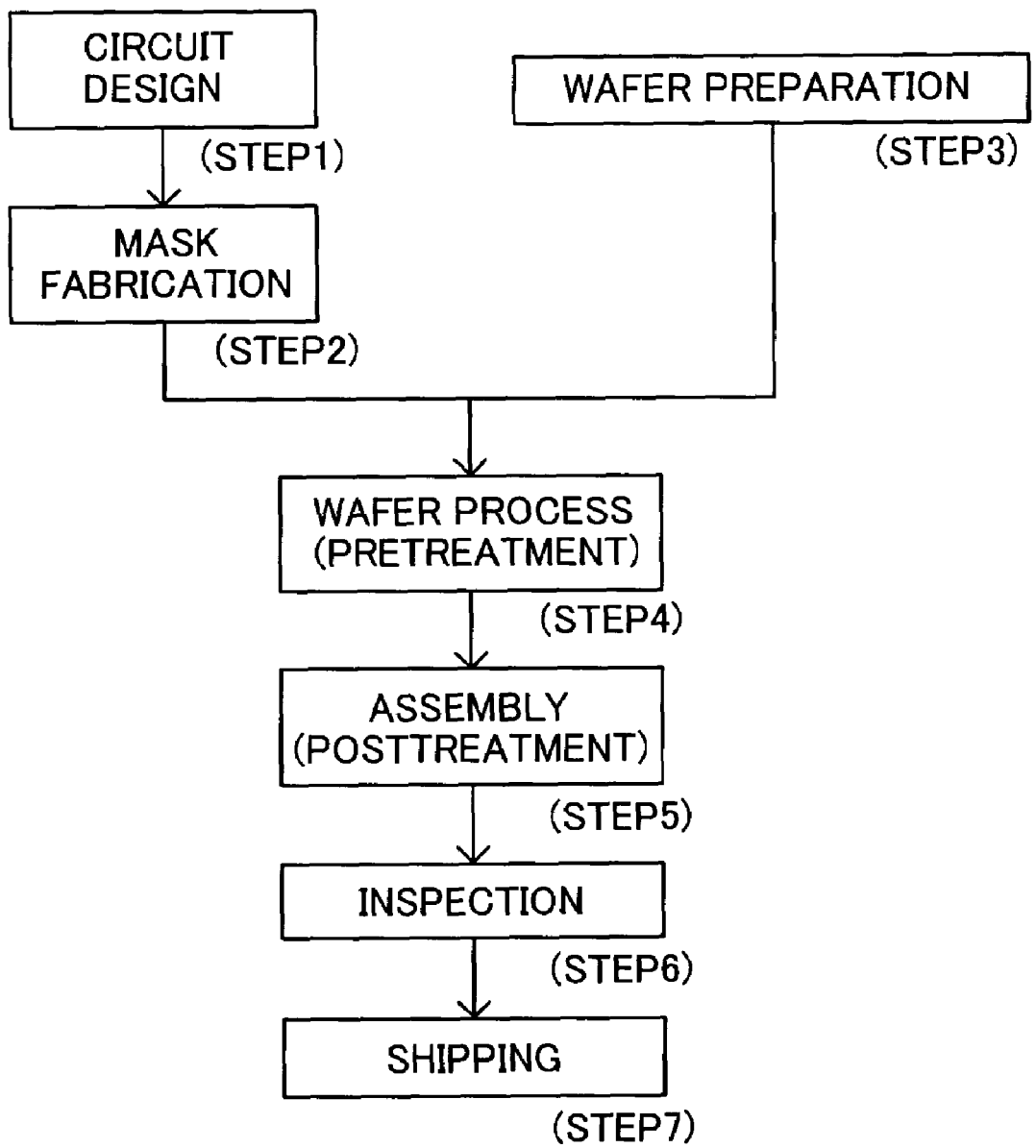
FIG. 27 is a flowchart for explaining how to fabricate devices (such as semiconductor chips such as ICs and LCDs, CCDs, and the like).
Figure 28:
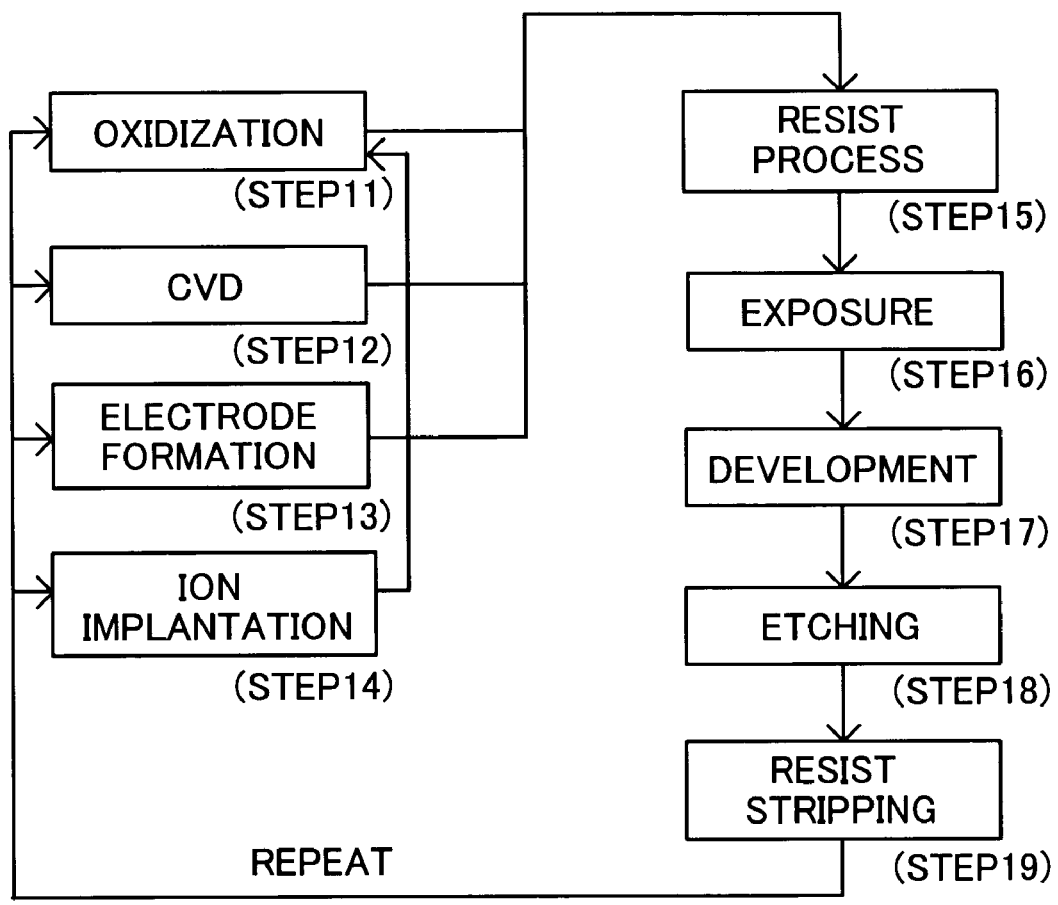
FIG. 28 is a detail flowchart of a wafer process as Step 4 shown in FIG. 27.

Referring now to FIGS. 27 and 28, a description will be given of an embodiment of a device fabricating method using the above exposure apparatus. FIG. 27 is a flowchart for explaining a fabrication of devices (i.e., semiconductor chips such as IC and LSI, LCDs, CCDs, etc.). Here, a description will be given of a fabrication of a semiconductor chip as an example. Step 1 (circuit design) designs a semiconductor device circuit. Step 2 (mask fabrication) forms a mask having a designed circuit pattern. Step 3 (wafer preparation) manufactures a wafer using materials such as silicon. Step 4 (wafer process), which is referred to as a pretreatment, forms actual circuitry on the wafer through photolithography using the mask and wafer. Step 5 (assembly), which is also referred to as a posttreatment, forms into a semiconductor chip the wafer formed in Step 4 and includes an assembly step (e.g., dicing, bonding), a packaging step (chip sealing), and the like. Step 6 (inspection) performs various tests for the semiconductor device made in Step 5, such as a validity test and a durability test.

Through these steps, a semiconductor device is finished and shipped (Step 7).

FIG. 28 is a detailed flowchart of the wafer process in Step 4 in FIG. 27. Step 11 (oxidation) oxidizes the wafer's surface. Step 12 (CVD) forms an insulating film on the wafer's surface. Step 13 (electrode formation) forms electrodes on the wafer by vapor disposition and the like. Step 14 (ion implantation) implants ion into the wafer. Step 15 (resist process) applies a photosensitive material onto the wafer. Step 16 (exposure) uses the exposure apparatus to expose a circuit pattern on the mask onto the wafer. Step 17 (development) develops the exposed wafer. Step 18 (etching) etches parts other than a developed resist image. Step 19 (resist stripping) removes disused resist after etching. These steps are repeated, and multilayer circuit patterns are formed on the wafer.

Further, the present invention is not limited to these preferred embodiments, and various modifications and changes may be made in the present invention without departing from the spirit and scope thereof.

Thus, the present invention may provide a birefringence measurement apparatus that may easily and accurately measure the retardation magnitude of an optical element, and a strain remover that may shorten the heat treatment time to remove the residual birefringence in the element, as well as controlling the retardation magnitude.

What is claimed is:

1. A birefringence measurement apparatus for calculating information of polarization of light emitted from an object to be measured, said birefringence measurement apparatus comprising:
a first polarization element for extracting a beam in a specific polarization direction of light emitted from a light source and directing the beam to the object;
at least one beam splitting unit that splits the light emitted from the object into two beams having the same polarization as that of the light emitted from the object;
at least two second polarization elements for extracting beams in a specific polarization direction of the light split by said beam splitting unit;
at least two light-quantity detectors for detecting light quantity of beams that have transmitted through the second polarization elements; and
an operation part for operating a light quantity received by said light-quantity detectors,
wherein the beam splitting unit includes:
a first plate inclining to the light emitted from the object, and splitting the light emitted from the object into a transmitted light and a reflected light;
a second plate inclining to the reflected light from said first plate, and splitting the reflected light from said first plate into a transmitted light and a reflected light; and
a third plate inclining to the transmitted light from said first plate, and splitting the transmitted light from said first plate into a transmitted light and a reflected light,
wherein said second plate is arranged so that p-polarized component which has reflected upon said first plate reflects as s-polarized component on said second plate, said third plate is arranged so that p-polarized component which has transmitted through said first plate transmits as s-polarized component through said third plate, and
the two beams having the same polarization as that of the light emitted from the object are the reflected light from said second plate and the transmitted light from said third plate.

2. A birefringence measurement apparatus according to claim 1, wherein the light source uses pulsed light.

3. A birefringence measurement apparatus according to claim 2, wherein the light source is an excimer laser.

4. A birefringence measurement apparatus according to claim 1, wherein the first polarization element includes a linear polarizer.

5. A birefringence measurement apparatus according to claim 1, further comprising a rotating mechanism for rotating the first polarization element around an optical axis.

6. A birefringence measurement apparatus according to claim 5, wherein said birefringence measurement apparatus calculates a retardation magnitude and an azimuth of a principal axis of the object retardance by feeding back polarization changes of the light emitted from the object, which has been analyzed by said operation part, to the rotating mechanism.

7. A birefringence measurement apparatus according to claim 1, further comprising a rotating mechanism for rotating the object around an optical axis.

8. A birefringence measurement apparatus according to claim 7, wherein the light source uses pulsed light.

9. A birefringence measurement apparatus according to claim 7, wherein the light source is an excimer laser.

10. A birefringence measurement apparatus according to claim 1, further comprising a measurement position varying mechanism for varying a measurement point of the object.

11. A birefringence measurement apparatus according to claim 1, further comprising a mechanism for inserting the object into and removing the object from the beam to be measured.

12. A birefringence measurement apparatus according to claim 1, wherein the beam splitting unit splits incident light into at least two beams while maintaining polarization of the incident light.

13. A birefringence measurement apparatus according to claim 1, wherein the second polarization element is a linear polarizer.

14. A birefringence measurement apparatus according to claim 1, further comprising a rotating mechanism for rotating the second polarization elements around an optical axis.

15. A birefringence measurement apparatus according to claim 1, wherein the second polarization elements are in crossed nicols to the first polarization element.

16. A birefringence measurement apparatus according to claim 1, wherein the second polarization elements are in parallel nicols to the first polarization element.

17. A birefringence measurement apparatus according to claim 1, wherein the operation part analyzes polarization changes of the light emitted from the object based on an output result of the light-quantity detector to the rotational angle of the object.

18. A birefringence measurement apparatus according to claim 1, wherein the operation part analyzes polarization changes of the light emitted from the object based on an output result of light-quantity detector to rotational angles of the first and second polarization elements.

19. A birefringence measurement apparatus according to claim 1, wherein said birefringence measurement apparatus calculates a retardation magnitude and an azimuth of a principal axis of the object retardance based on polarization changes of the light emitted from the object, which has been analyzed by said operation part.

20. A birefringence measurement apparatus according to claim 1, further comprising a rotating mechanisms for rotating the first and second polarization elements, wherein said birefringence measurement apparatus calculates a retardation magnitude and an azimuth of a principal axis of the object retardance by feeding back polarization changes of the light emitted from the object, which has been analyzed by said operation part, to the rotating mechanism.

21. A strain remover that removes strain of an optical element generated during a manufacture process of the optical element, said strain remover comprising:

a heat treatment part that heat treats the optical element; and a birefringence measurement apparatus for calculating information of polarization of light emitted from the optical element, said birefringence measurement apparatus comprising:

a first polarization element for extracting a beam in a specific polarization direction of light from a light source and directing the beam to the optical element;

at least one beam splitting unit that splits the light emitted from the optical element into two beams having the same polarization as that of the light emitted from the optical element;

at least two second polarization elements for extracting beams in a specific polarization direction of the light split by said beam splitting unit;

at least two light-quantity detectors for detecting light quantity of the beam that has transmitted through the second polarization elements; and an operation part for operating a light quantity received by said light-quantity detectors, wherein the beam splitting unit includes:

a first plate inclining to the incident light and splitting the incident light into a transmitted light and a reflected light;

a second plate inclining to the reflected light from said first plate, and splitting the reflected light from said first plate into a transmitted light and a reflected light, and a third plate inclining to the transmitted light from said first plate, and splitting the transmitted light from said first plate into a transmitted light and a reflected light wherein said second plate is arranged so that p-polarized component which has reflected upon said first plate reflects as s-polarized component on said second plate, said third plate is arranged so that p-polarized component which has transmitted through said first plate transmits as s-polarized component through said third plate, and the two beams having the same polarization as the incident light are the reflected light from said second plate and the transmitted light from said third plate.

22. A strain remover according to claim 21, further comprising a controller that controls heat treatment conditions for the optical element so that retardation magnitude of the optical element is within a predetermined range, by measuring the retardation magnitude of the optical element during the heat treatment and feeding back the heat treatment part.

23. A polarimeter that calculates polarization information of incident light, said polarimeter comprising:

at least one beam splitting unit that splits the incident light into two beams having the same polarization as the incident light;

at least two polarization elements for extracting beams in a specific polarization direction of the light split by said beam splitting unit;

a rotary mechanism for rotationally controlling the polarization elements;

at least two light-quantity detectors for detecting light quantity of beams that have transmitted through the polarization elements; and an operation part that operates light quantity received by the light-quantity detector, wherein the beam splitting unit includes:

a first plate inclining to the incident light and splitting the incident light into a transmitted light and a reflected light;

a second plate inclining to the reflected light from said first plate, and splitting the reflected light from said first plate into a transmitted light and a reflected light, and a third plate inclining to the transmitted light from said first plate, and splitting the transmitted light from said first plate into a transmitted light and a reflected light wherein said second plate is arranged so that p-polarized component which has reflected upon said first plate reflects as s-polarized component on said second plate, said third plate is arranged so that p-polarized component which has transmitted through said first plate transmits as s-polarized component through said third plate, and the two beams having the same polarization as the incident light are the reflected light from said second plate and the transmitted light from said third plate.

* * * * *